(12) United States Patent
Kadrmas et al.

(10) Patent No.: US 7,848,557 B2
(45) Date of Patent: Dec. 7, 2010

(54) RAPID MULTI-TRACER PET IMAGING SYSTEMS AND METHODS

(75) Inventors: Dan J. Kadrmas, North Salt Lake, UT (US); Edward V. R. DiBella, Salt Lake City, UT (US); Noel F. Black, Salt Lake City, UT (US); Thomas C. Rust, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 928 days.

(21) Appl. No.: 11/690,178

(22) Filed: Mar. 23, 2007

(65) Prior Publication Data

US 2008/0230703 A1    Sep. 25, 2008

(51) Int. Cl.
    *G06K 9/00* (2006.01)
(52) U.S. Cl. .......................................... 382/131; 378/4
(58) Field of Classification Search ................. 382/128, 382/131; 378/4, 21; 250/363.03, 363.04
    See application file for complete search history.

(56) References Cited

U.S. PATENT DOCUMENTS

| | | | |
|---|---|---|---|
| 6,161,031 A | 12/2000 | Hochman et al. | |
| 6,628,743 B1 | 9/2003 | Drummond et al. | |
| 6,661,866 B1 | 12/2003 | Limkeman et al. | |
| 7,022,077 B2 | 4/2006 | Mourad et al. | |
| 7,126,126 B2 | 10/2006 | Schyler et al. | |
| 7,127,095 B2 | 10/2006 | Fakhri et al. | |
| 7,180,074 B1 | 2/2007 | Crosetto | |
| 2003/0211036 A1* | 11/2003 | Degani et al. | 424/1.11 |
| 2005/0082486 A1 | 4/2005 | Schlyer et al. | |
| 2005/0113667 A1 | 5/2005 | Schlyer et al. | |
| 2006/0025658 A1 | 2/2006 | Newman et al. | |
| 2006/0228296 A1* | 10/2006 | Dive et al. | 424/1.11 |
| 2006/0261279 A1 | 11/2006 | Crosetto | |
| 2006/0269130 A1* | 11/2006 | Maroy et al. | 382/173 |
| 2007/0014463 A1 | 1/2007 | Fakhri et al. | |
| 2007/0020178 A1* | 1/2007 | Weichert et al. | 424/1.11 |
| 2007/0218002 A1* | 9/2007 | Barrio et al. | 424/9.1 |
| 2009/0226064 A1* | 9/2009 | El Fakhri et al. | 382/128 |

OTHER PUBLICATIONS

Sharp, et al.; "Techniques necessary for multiple tracer quantititative small-animal imaging studies"; Nucl Med Biol; Nov. 2005; website: http://www.ncbi.nlm.nih.gov.

Dorow, et al.; "Multi-tracer small animal PET imaging of the tumour response to the novel pan-Erb-B inhibitor CI-1033"; Eur J Nucl Med Mol Imaging; Apr. 2006; website: http://www.ncbi.nlm.nih.gov.

(Continued)

*Primary Examiner*—Matthew C Bella
*Assistant Examiner*—Shervin Nakhjavan
(74) *Attorney, Agent, or Firm*—Ballard Spahr LLP

(57) ABSTRACT

Methods are provided for recovering component signals or estimates of component signals from combined signals of multiple tracers in the context of imaging multiple PET tracers, a single tracer injected repeatedly, or a combination of tracers using multiple-timepoint or dynamic scanning, where the tracer administrations are simultaneous or staggered in time such that some or all of the PET timeframes, images, data, and/or datasets contain overlapping signals from more than one of the tracer administrations.

37 Claims, 12 Drawing Sheets

OTHER PUBLICATIONS

Wikipedia Encyclopedia; "Positron Emission Tomography"; website: http://en.wikipedia.org/wiki/Positron_emission_tomography; pp. 1-7.

Rust, et al.; "Rapid dual-injection single-scan $^{13}$N-ammonia PET for quantification of rest and stress myocardial blood flows"; IOP Publishing Ltd.; Institute of Physics Publishing; Physic in Medicine and Biology; vol. 51; 2006; pp. 5347-5362.

Rust, et al.; "Rapid dual-tracer PTSM+ATSM PET imaging of tumour blood flow and hypoxia: a simulation study"; Institute of Physics Publishing; Physic in Medicine and Biology; vol. 51; 2006; pp. 61-75.

Kadrmas, et al.; "Feasibility of Rapid Multitracer PET Tumor Imaging"; IEEE Transactions on Nuclear Science; vol. 52; No. 5; Oct. 2005; pp. 1341-1347.

* cited by examiner

BACKGROUND SUBTRACTION METHOD

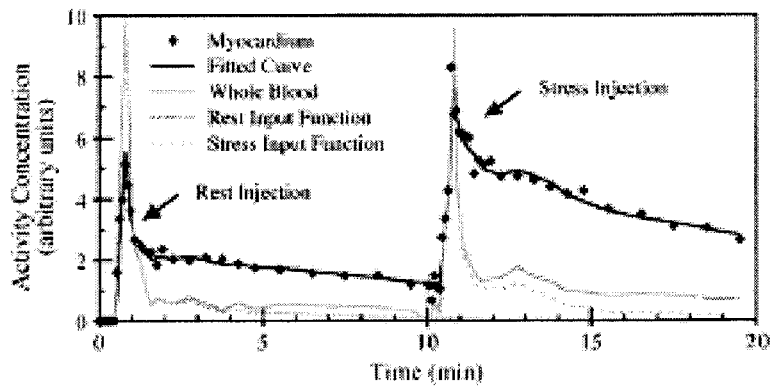
FIGURE 5
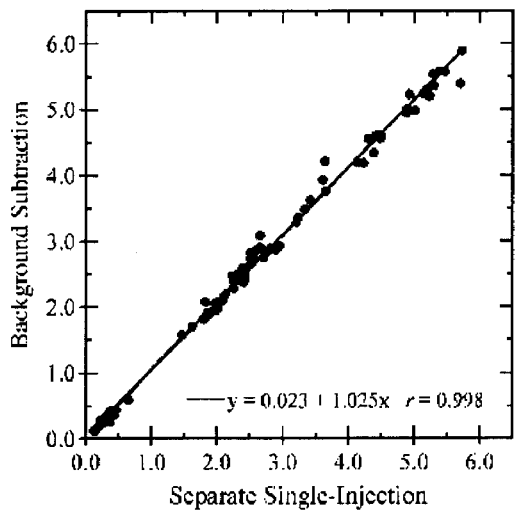
FIGURE 6
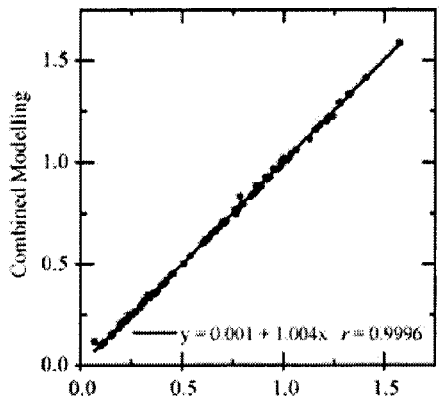 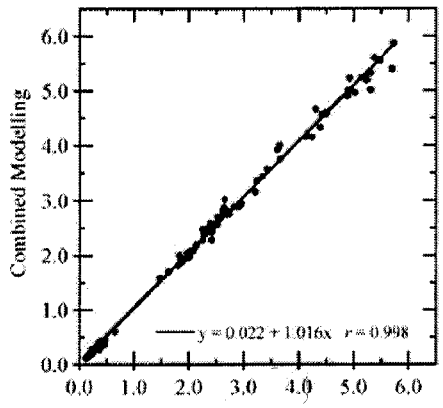
FIGURE 7A FIGURE 7B

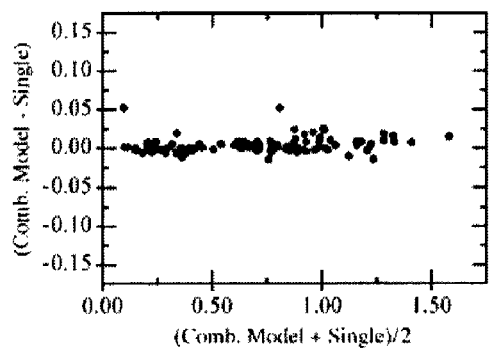 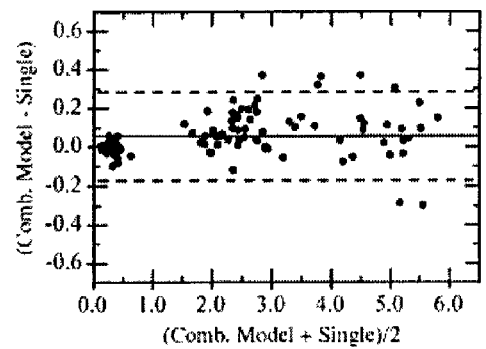
FIGURE 8A          FIGURE 8B
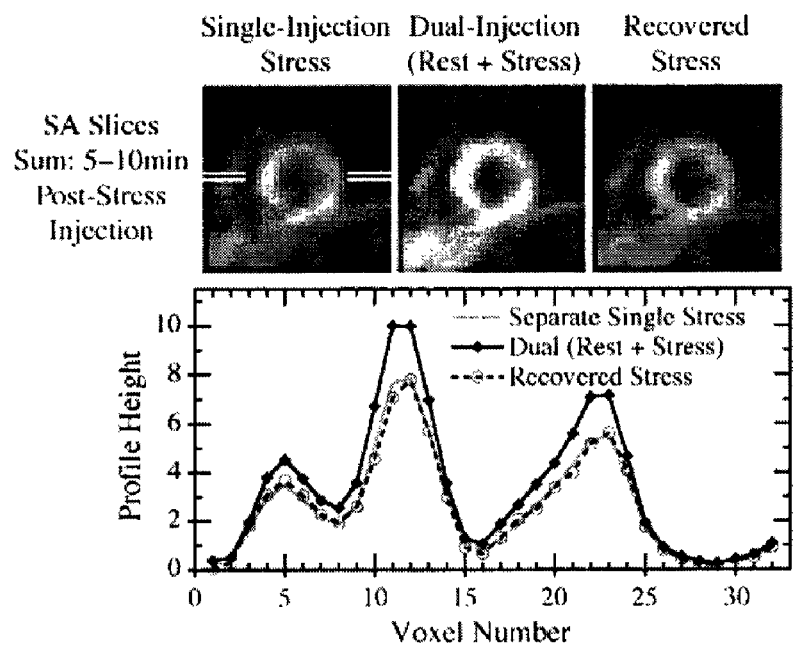
FIGURE 9

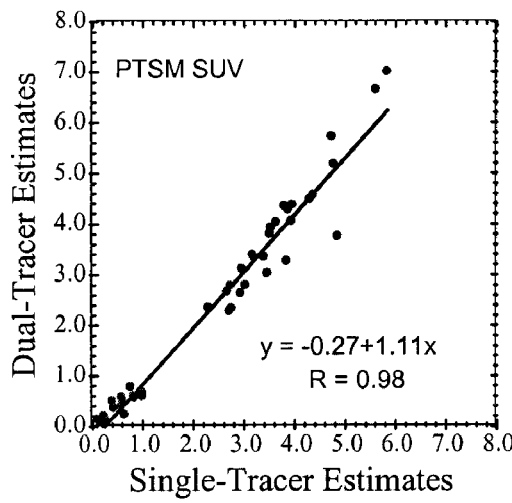
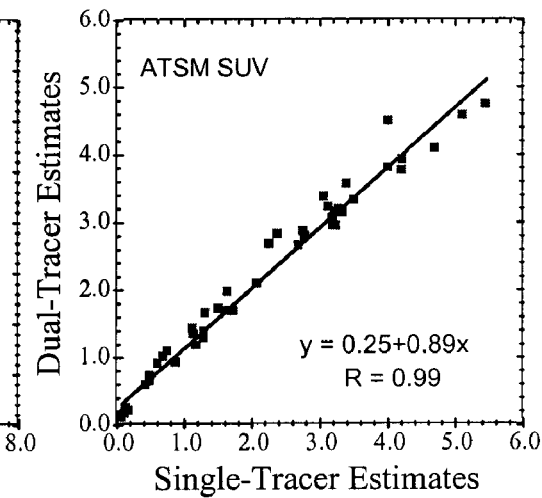
FIGURE 17A      FIGURE 17B
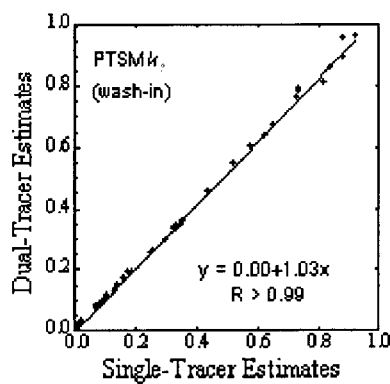
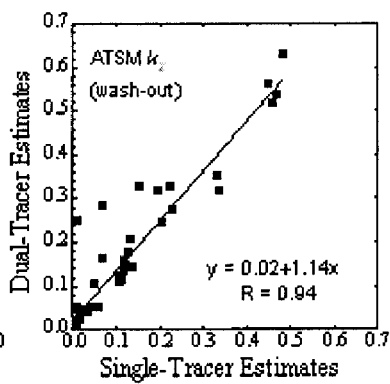
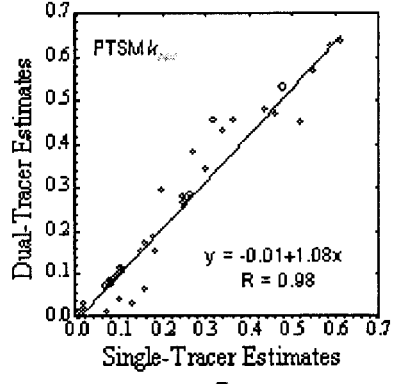
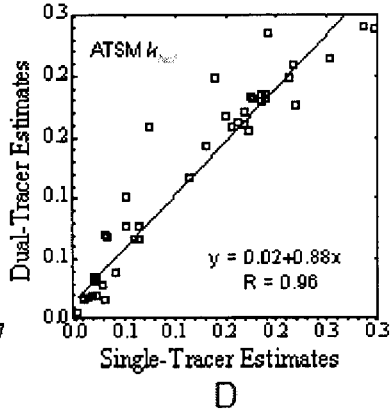
FIGURES 18A-18D

RAPID MULTI-TRACER PET IMAGING SYSTEMS AND METHODS

BACKGROUND

The present invention relates to the art of diagnostic imaging. In particular, it relates to positron emission tomography (PET) and other diagnostic modes in which a subject is examined and an image of the subject is reconstructed from information obtained during the examination.

Previously, PET has been used to study a radionuclide distribution in subjects. Typically, one or more radiopharmaceuticals (i.e., tracers) are injected into a subject. The radiopharmaceuticals are commonly injected into the subject's blood stream for imaging the circulatory system or for imaging specific organs which absorb the injected radiopharmaceuticals. PET is a physiologic imaging modality that images the distribution of radiolabeled tracers within the body. Unlike anatomic imaging modalities, which image tissue structures and morphology, PET can characterize the functional, metabolic, and physiologic status of tissues in vivo. Hundreds, if not thousands, of radiotracers have been investigated for PET, targeting parameters such as glucose metabolism, blood flow, hypoxia, cellular proliferation, amino acid synthesis, gene expression, and so on. As more is learned about the molecular bases for disease and treatment, PET becomes an increasingly powerful modality for characterizing and monitoring disease.

In some instances a subject must undergo multiple injections of a tracers and scans associated with each tracer. Subsequent injections may be the same tracer as the first, or they may each be a different tracer. Prior to each injection sufficient time must elapse to allow the earlier introduced tracer to flush from the subject or to decay. This decreases throughput of patients and is inconvenient for patients in clinical applications. To alleviate some of these challenges, rapid multi-tracer PET has been investigated. For instance, rate parameters for individual tracers have been recovered from data with overlapping signals from different PET tracers based on different half-lives, tracer kinetics, or both (Huang et al. 1982; Koeppe et al 1998 and 2001; Converse et al. 2004 and Kadrmas and Rust 2005). In 1982, Huang et al. demonstrated in a phantom that, when imaging static distributions of multiple PET tracer with different half-lives, images of each tracer can be recovered based on their different rates of radioactive decay. In short, this amounts to treating the dynamic PET signal as a sum of exponentials with known decay constants and estimating the coefficients of each exponential. While an important contribution, this approach has little or no practical application because (i) PET tracers are rarely static, except for irreversible tracers long after injection; and (ii) separation of summed exponentials is a poorly conditioned problem sensitive to statistical noise—requiring long scan durations relative to the half-lives of the tracers used in order to get acceptable results. In 1998, Koeppe et al. recovered kinetic rate parameters for two $^{11}$C-labeled brain tracers injected 10-30 minutes apart with a single dynamic PET scan. Though the multi-tracer PET signal was not separated into individual tracer components in this work and images of each tracer were not recovered, it did demonstrate recovery of certain rate parameters from a dual-tracer dataset.

However, these earlier works have not resulted in the recreation of activity timecourses for each individual tracer from combine tracer data nor have they allowed the creation of an image from combined tracer data obtained in a single scan.

Therefore, what is needed is a means to overcome challenges found in the art, some of which are described above.

SUMMARY

Described herein are embodiments of methods for recovering component signals or estimates of component signals from combined signals of multiple tracers in the context of imaging multiple PET tracers, a single tracer injected repeatedly, or a combination of tracers using multiple-timepoint or dynamic scanning, where the tracer administrations are simultaneous or staggered in time such that some or all of the PET timeframes, images, data, and/or datasets contain overlapping signals from more than one of the tracer administrations.

In one aspect, a method of recovering individual tracer signals from multi-tracer PET data is provided. The method comprises introducing a first tracer into a subject and introducing at least a second tracer into the subject. Multi-tracer PET data of the subject is obtained by performing a PET scan of the subject beginning with or subsequent to introducing the first tracer, and covering at least in part times when at least one or more additional tracers have been introduced. The multi-tracer PET data is applied against a multi-tracer kinetic model or other kinetic constraint to estimate individual tracer signals for each individual tracer at one or more timepoints based upon a fit of the multi-tracer PET data to the multi-tracer kinetic model or other kinetic constraint. The multi-tracer kinetic model estimates parameters or a time-dependent activity timecourse for each of said first and at least second tracer. This method can be applied to cancer imaging, among other uses.

In another aspect, a method of recovering individual tracer signals from multi-tracer PET data for rest/stress cardiac imaging is provided. This method comprises introducing a first tracer into a subject during cardiac rest and introducing a second tracer into the subject during cardiac stress. Multi-tracer PET data of the subject is obtained by performing a cardiac PET scan of the subject subsequent to introducing the first tracer and the second tracer into the subject. The cardiac multi-tracer PET data includes cardiac rest first tracer data and cardiac stress second tracer data. A multi-tracer kinetic model is provided. The multi-tracer kinetic model estimates time-dependent kinetic parameters or a time-dependent activity timecourse for each of the first and second tracers. The multi-tracer kinetic model is applied to the cardiac multi-tracer PET data and individual tracer signals are estimated for each individual tracer at one or more timepoints based upon a fit of the multi-tracer PET data to the multi-tracer kinetic model. The fit to the multi-tracer kinetic model can recover parameters of interest for each tracer. In addition, constraints from the multi-tracer kinetic model can be applied to individual voxels or groups of voxels to recover dynamic or static cardiac images for each tracer.

Additional advantages of the invention will be set forth in part in the description which follows or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are not to scale and are incorporated in and constitute a part of this specification, illustrate embodiments according to the invention and together with the description, serve to explain the principles of the invention:

FIG. 5 is a typical example of emulated rapid dual-injection data as used in the methods described herein;

FIG. 6 provides a direct comparison of the stress MBF estimates for an embodiment of the present invention (the background subtraction method) versus separate single-injection results for each myocardial region;

FIGS. 7A and 7B compare rest (A) and stress (B) blood flow estimates obtained from rapid dual-injection data according to an embodiment of the present invention using combined modeling versus the separate single-injection standards;

FIGS. 8A and 8B analyze the small differences in values obtained from the two methods compared in FIGS. 7A and 7B;

FIG. 9 shows a conventional short-axis stress image, the dual-injection image containing both rest and stress components, and the stress image recovered according to an embodiment of the present invention;

FIGS. 17A and 17B show scatters plots of SUVs for PTSM and ATSM recovered from dual-tracer data versus the single-tracer standards;

FIGS. 18A-18D shows the results for kinetic parameter estimates according to an embodiment of the present invention.

DETAILED DESCRIPTION

Figure 1A:
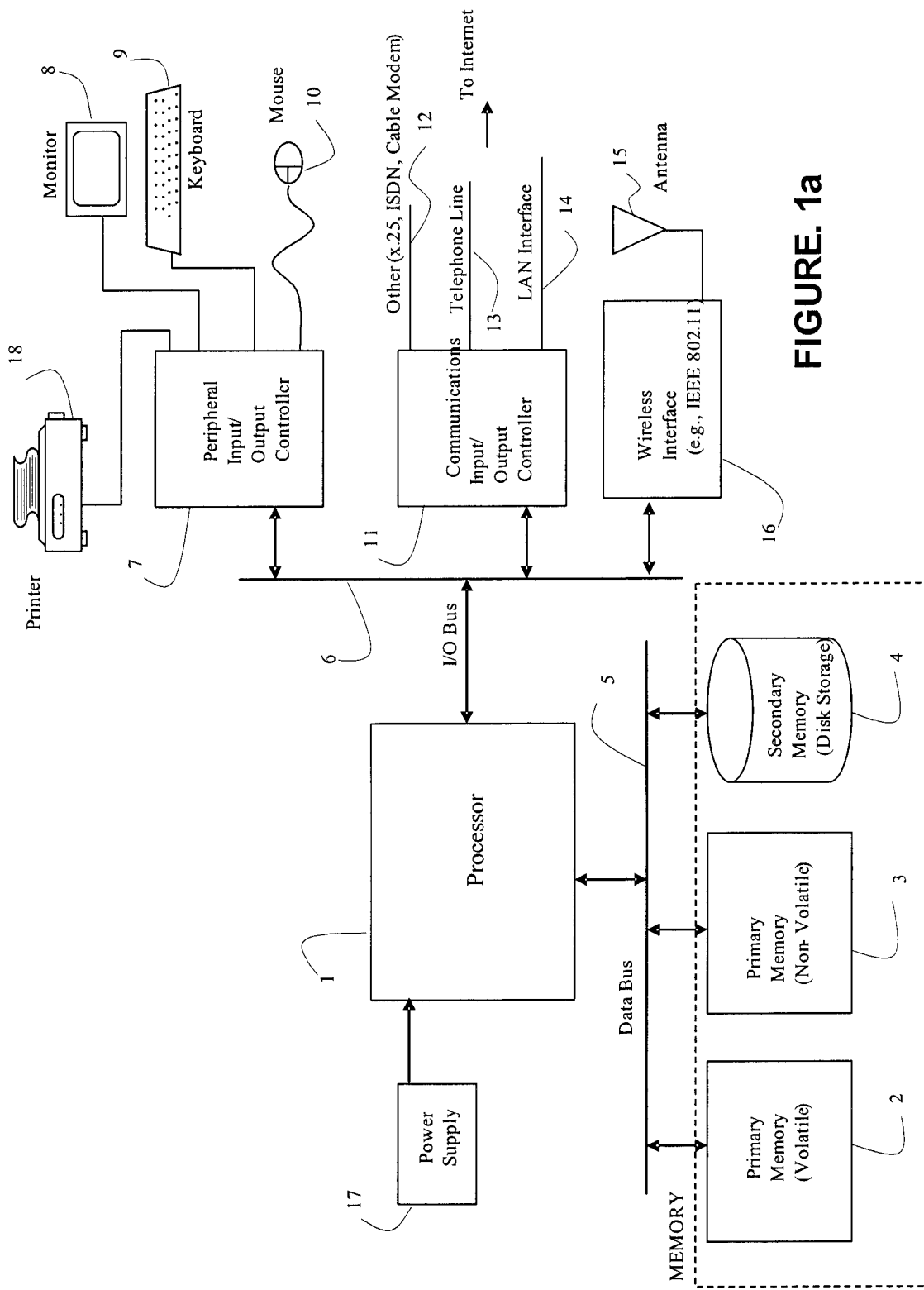
FIG. 1a is an illustration of an embodiment of a computing device that can be used to practice aspects of the present invention.

Before the present methods and systems are disclosed and described, it is to be understood that this invention is not limited to specific synthetic methods, specific components, or to particular compositions, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

The present invention may be understood more readily by reference to the following detailed description of preferred embodiments according to the invention and the Examples included therein and to the Figures and their previous and following description.

Herein, the term "tracer" is used to identify each individual tracer or administration of a tracer, and will be used generically to refer to both tracers of different chemical form and multiple administrations of the same tracer at different times and/or under different physiological conditions (e.g. at rest and stress for myocardial perfusion imaging).

Likewise, the term "multi-tracer" refers to data containing contributions from more than one tracer as defined above (such that rapid sequential rest/stress myocardial perfusion imaging constitutes multi-tracer imaging in that there are two tracer administrations—one at rest and another at stress—wherein a part of the PET data contains signals arising from both tracer administrations).

The term PET "signal"" is broadly used to describe the essence of the PET measurement under discussion. To varying degrees multi-tracer PET signal separation can be performed on the raw scanner data, partially processed data, reconstructed dynamic images, and/or time-activity curves; similarly, for each tracer, the imaging endpoint(s) may be a static image, standardized uptake value (SUV), pseudo-quantitative measure, kinetic parameter(s) and/or macro parameter(s). For a given dataset and imaging endpoint, "signal" is used to identify the element or elements of the dataset necessary for computing the desired endpoint. Likewise, "signal separation" (and "signal recovery") refer to the process of separating a multi-tracer dataset into individual tracer components, thereby recovering the necessary signal for each tracer for computing the desired endpoint.

As will be appreciated by one skilled in the art, the preferred embodiment may be implemented as a method, a data processing system, or a computer program product. Accordingly, the preferred embodiment may take the form of an entirely hardware embodiment, an entirely software embodiment, or an embodiment combining software and hardware aspects. Furthermore, implementations of the preferred embodiment may take the form of a computer program product on a computer-readable storage medium having computer-readable program instructions (e.g., computer software) embodied in the storage medium. More particularly, implementations of the preferred embodiments may take the form of web-implemented computer software. Any suitable computer-readable storage medium may be utilized including hard disks, CD-ROMs, optical storage devices, or magnetic storage devices.

The preferred embodiments according to the present invention are described below with reference to block diagrams and flowchart illustrations of methods, apparatuses (i.e., systems) and computer program products according to an embodiment of the invention. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Computer or Computing Device

In the embodiments referenced herein, a "computer" or "computing device" may be referenced. Such computer may be, for example, a mainframe, desktop, notebook or laptop, a hand held device such as a data acquisition and storage device, or it may be a processing device embodied within another apparatus such as, for example, a scanner used for tomography. In some instances the computer may be a "dumb" terminal used to access data or processors over a network. Turning to FIG. 1a, one embodiment of a computing device is illustrated that can be used to practice aspects of the preferred embodiment. In FIG. 1a, a processor 1, such as a microprocessor, is used to execute software instructions for carrying out the defined steps. The processor 1 receives power from a power supply 17 that also provides power to the other components as necessary. The processor 1 communicates using a data bus 5 that is typically 16 or 32 bits wide (e.g., in parallel). The data bus 5 is used to convey data and program instructions, typically, between the processor and memory. In the present embodiment, memory can be considered primary memory 2 that is RAM or other forms which retain the contents only during operation, or it may be non-volatile 3, such as ROM, EPROM, EEPROM, FLASH, or other types of memory that retain the memory contents at all times. The memory could also be secondary memory 4, such as disk storage, that stores large amount of data. In some embodiments, the disk storage may communicate with the processor using an I/O bus 6 instead or a dedicated bus (not shown). The secondary memory may be a floppy disk, hard disk, compact disk, DVD, or any other type of mass storage type known to those skilled in the computer arts.

The processor 1 also communicates with various peripherals or external devices using an I/O bus 6. In the present embodiment, a peripheral I/O controller 7 is used to provide standard interfaces, such as RS-232, RS422, DIN, USB, or other interfaces as appropriate to interface various input/output devices. Typical input/output devices include local printers 18, a monitor 8, a keyboard 9, and a mouse 10 or other typical pointing devices (e.g., rollerball, trackpad, joystick, etc.).

The processor 1 typically also communicates using a communications I/O controller 11 with external communication networks, and may use a variety of interfaces such as data communication oriented protocols 12 such as X.25, ISDN, DSL, cable modems, etc. The communications controller 11 may also incorporate a modem (not shown) for interfacing and communicating with a standard telephone line 13. Finally, the communications I/O controller may incorporate an Ethernet interface 14 for communicating over a LAN. Any of these interfaces may be used to access a wide area network such as the Internet, intranets, LANs, or other data communication facilities.

Finally, the processor 1 may communicate with a wireless interface 16 that is operatively connected to an antenna 15 for communicating wirelessly with another device, using for example, one of the IEEE 802.11 protocols, 802.15.4 protocol, or a standard 3G wireless telecommunications protocols, such as CDMA2000 1x EV-DO, GPRS, W-CDMA, or other protocol.

Figure 1B:
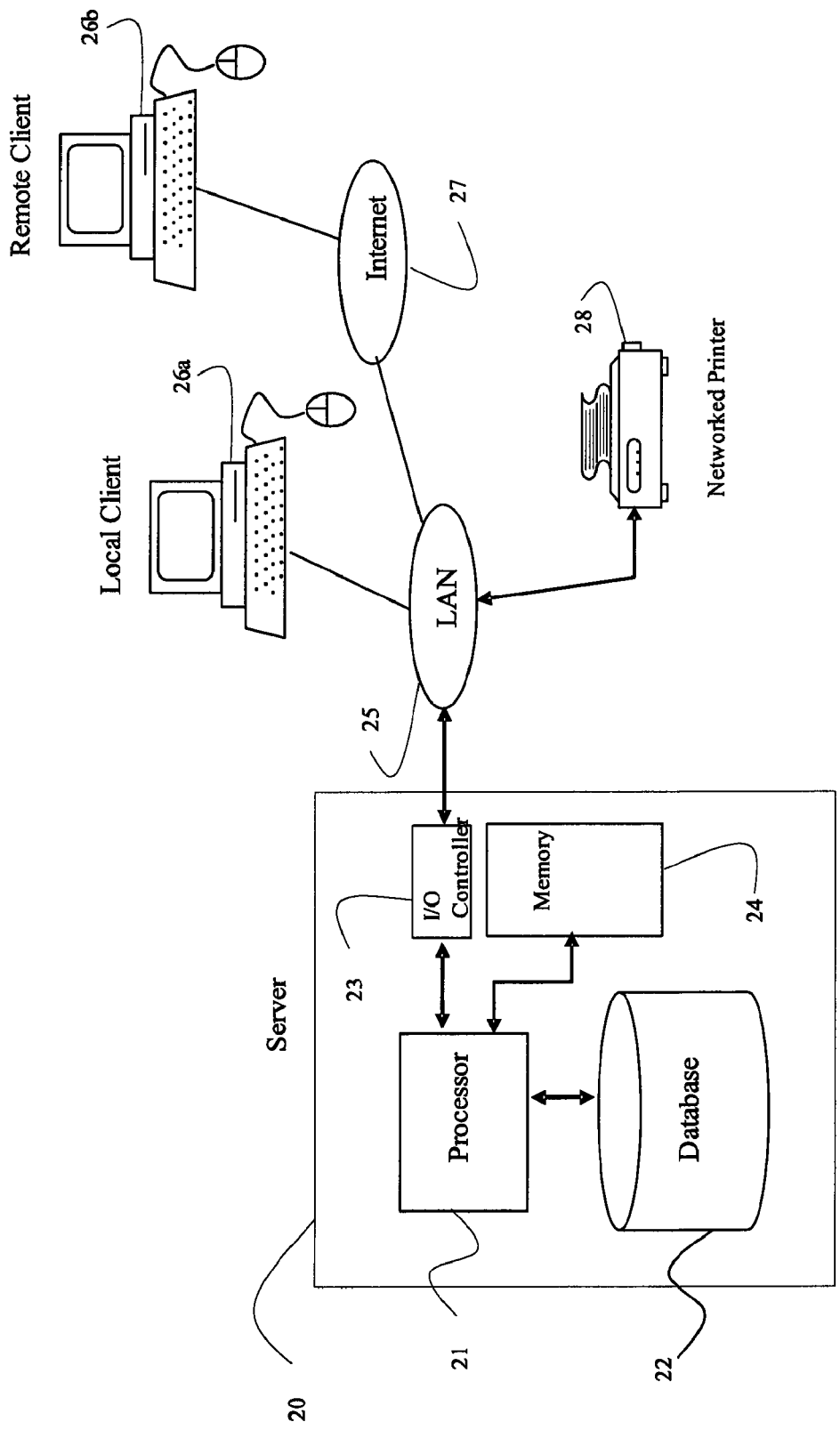
FIG. 1b is an alternative embodiment of a processing system that may be used to practice aspects of the present invention.

An alternative embodiment of a processing system that may be used is shown in FIG. 1b. In this embodiment, a distributed communication and processing architecture is shown involving a server 20 communicating with either a local client computer 26a or a remote client computer 26b. The server 20 typically comprises a processor 21 that communicates with a database 22, which can be viewed as a form of secondary memory, as well as primary memory 24. The processor also communicates with external devices using an I/O controller 23 that typically interfaces with a LAN 25. The LAN may provide local connectivity to a networked printer 28 and the local client computer 26a. These may be located in the same facility as the server, though not necessarily in the same room. Communication with remote devices typically is accomplished by routing data from the LAN 25 over a communications facility to a wide area network 27, such as the Internet. A remote client computer 26b may execute a web browser, so that the remote client 26b may interact with the server as required by transmitted data through the wide area network 27, over the LAN 25, and to the server 20.

Those skilled in the art of data networking will realize that many other alternatives and architectures are possible and can be used to practice the preferred embodiments. The embodiments illustrated in FIGS. 1a and 1b can be modified in different ways and be within the scope of the present invention as claimed.

Overview

Described herein are embodiments of a method of recovering component signals or estimates of component signals from combined signals of multiple tracers in the context of imaging multiple PET tracers, a single tracer injected repeatedly, or a combination of tracers using multiple-timepoint or dynamic scanning, where the tracer administrations are simultaneous or staggered in time such that some or all of the PET timeframes, images, data, and/or datasets contain overlapping signals from more than one of the tracer administrations.

A number of algorithms for separating multi-tracer PET datasets into individual-tracer components are provided herein, where the recovered data for each tracer can be subsequently analyzed by conventional single-tracer methods. These algorithms include background subtraction and model-based signal separation comprised of model-guided signal separation and model-restricted signal separation. Each of the multi-tracer signal separation algorithms utilizes models or analysis methods that describe the dynamic behavior of the tracers; in general these kinetic models are well understood for single-tracer imaging, but generally have not been applied to multi-tracer PET. Without loss of generality, some of the algorithms are presented in the context of dual-tracer imaging to improve clarity, though each method can generally be extended to three or more tracers as desired. Also, without loss of generality, the signal will often be described as a time-activity curve in this discussion since the concepts are generally more easily present in that context. However, it is to be appreciated that single-tracer kinetic analysis methods have been applied in both projection space and image space, and that multi-tracer kinetic models and signal separation algorithms can likewise be applied in the same manners and should not be construed to be limited in application to time-activity curves per se.

Multi-Tracer Signal Separation Algorithms

The general premise for multi-tracer signal separation is that the kinetic behavior of each tracer obeys certain constraints—and when staggered injections are used, these constraints provide sufficient information to recover the signal components due to each tracer from the overlapping portions of the time-activity curves.

Let $R_{multi}(t)$ represent the PET signal at time t, including contributions from all tracers present. Since the signals from each individual tracer are not explicitly distinguishable:

$$R_{multi}(t) = \sum_{n=1}^{N} R_n(t), \quad (1)$$

where $R_n(t)$ is the signal from tracer n, and N is the number of tracers. In general, the process of signal separation is to recover $R_n(t)$ for every n from $R_{multi}(t)$. In the following discussion, a tilde (~) is used to indicate that a variable is a (noisy) measured quantity, a bar (-) to indicate it is modeled, and a caret (^) to indicate that it is estimated or recovered.

I. Background Subtraction

Perhaps the simplest approach to dual-tracer signal separation is to treat the residual activity from the first tracer as a background behind the signal for the second tracer. If this background can be estimated from the single-tracer portion of the scan (i.e., from the data acquired from the time of injection of the first tracer up to the time of injection of the second), then it can be subtracted (or otherwise removed) from the overlapping portion of the data. Consider dual-tracer imaging with a first tracer (tracer 1) injected at time $T_1^{inj}$ and a second tracer (tracer 2) injected at time $T_2^{inj}$ (typically, $T_1^{inj}=0$ and $T_2^{inj}>0$). The dual-tracer signal can be written:

$$R_{multi}(t) = \begin{cases} R_1(t), & t < T_2^{inj} \\ R_1(t) + R_2(t), & t \geq T_2^{inj} \end{cases}. \quad (2)$$

Thus, $R_1(t)$ is directly measured for $0 \leq t < T_2^{inj}$ and the activity from tracer 1 can be extrapolated to times after injection of the second tracer, $\bar{R}_1^{ext}(t \geq T_2^{inj})$. A bar is used to indicate that $\bar{R}_1^{ext}$ is a modeled quantity, e.g. modeled from a fit to the data for $t < T_2^{inj}$. The background subtraction method treats $\bar{R}_1^{ext}(t \geq T_2^{inj})$ as a background on the measurement of $R_2(t)$, subtracting it to recover the signal for the second tracer.

Background Subtraction:

$$\hat{R}_1(t) = \begin{cases} \tilde{R}_{multi}(t), & t < T_2^{inj} \\ \bar{R}_1^{ext}(t), & t \geq T_2^{inj} \end{cases} \quad (3)$$

and $$\hat{R}_2(t) = \begin{cases} 0, & t < T_2^{inj} \\ \tilde{R}_{multi}(t) - \bar{R}_1^{ext}(t), & t \geq T_2^{inj} \end{cases}$$

$\tilde{R}_{multi}(t)$ is shown with a tilde to denote that the measurement is noisy. Inspection of equation (3) reveals that the recovered signal for tracer 1, $\hat{R}_1(t)$, contains all of the noise from the measurement for $t < T_2^{inj}$, but $t \geq T_2^{inj}$ receives no noise from the measurement other than noise contributions from $t < T_2^{inj}$ into $\bar{R}_1^{ext}(t)$. Since $\bar{R}_1^{ext}(t)$ is a modeled quantity, it "appears" noise free and $\hat{R}_1(t)$ changes smoothly in time for $t \geq T_2^{inj}$. On the other hand, $\hat{R}_2(t)$ contains all of the noise from the measurement at $t \geq T_2^{inj}$, and furthermore this noise is boosted in some sense as a result of subtracting off the background signal.

Background subtraction is better served when the signal from tracer 1 is sufficiently well-defined by the measurement from $0 \leq t < T_2^{inj}$ such that accurate extrapolation to times $t \geq T_2^{inj}$ can be performed, and the magnitude of the signal for tracer 2 is sufficiently large relative to that of tracer 1 for $t \geq T_2^{inj}$, such that the noise in $\hat{R}_2(t)$ is acceptable.

Signal Extrapolation Ignoring patient movement, misregistration, and other such effects, the extrapolated signal $\overline{R}_1^{ext}(t \geq T_2^{inj})$ can be accurately estimated when the first tracer is static at times $t \geq T_2^{inj}$ (or at equilibrium so there is no net flux of the tracer), or when the changing distribution of tracer 1 can be accurately predicted from the measurements at $0 \leq t < T_2^{inj}$. In the former case, the extrapolated signal need only account for radioactive decay and the extrapolation is trivial. In the latter case, some form of kinetic model or constraint needs to be applied to predict $\overline{R}_1^{ext}(t \geq T_2^{inj})$. This kinetic model can take the form of a compartment model or more generalized kinetic model, or other kinetic analysis procedure such as principal component analysis (PCA), frequency analysis of dynamic structures (FADS), spectral analysis, and others. Two example methods are presented here, compartment model-based signal extrapolation, and generic component-analysis based signal extrapolation, though it is to be appreciated that other methods are contemplated within the scope of this invention.

A. Signal Extrapolation by Compartment Modeling

Using compartment modeling, the activity concentration due to a single tracer in a PET voxel or region-of-interest (ROI) can be written:

$$R(t) = f_B B(t) + (1 - f_B) A(t) \quad (4)$$

where $f_B$ is the vascular fractional volume, $B(t)$ is the activity concentration in the whole blood, and $A(t)$ is the activity concentration in the extravascular tissue. Here, $A(t)$ depends on the input function $b(t)$, which is the activity concentration in the blood which is freely available to exchange with the tissue, the kinetic rate parameters of the compartment model $\{k_i\}$, and the radioactive decay constant $\lambda$. Note that, for multi-tracer PET, radioactive decay should be incorporated into the compartment model, such that $A(t)$, $B(t)$, and $R(t)$ all contain the effects of such decay (i.e., are not decay-corrected). This is so that radioactive decay can aid in the signal separation process.

When using background subtraction with compartment model-based signal extrapolation, the compartment model for tracer 1 is first fit to the measured data for $0 \leq t < T_2^{inj}$ to estimate $f_B$ and the rate parameters for tracer 1, $\{k_i\}_1$. This requires knowledge of the whole-blood activity concentration and input functions for tracer 1, $B_1(t)$ and $b_1(t)$ respectively (e.g. from arterial blood sampling). Assuming $B_1(t)$ and $b_1(t)$ are known for $t \geq T_2^{inj}$, the compartment model and fitted parameters are then used to predict $A_1^{ext}(t \geq T_2^{inj})$ and, via equation (4), $\overline{R}_1^{ext}(t \geq T_2^{inj})$. The signal separation can then be performed by application of equation (3). Any errors in the fitted parameters or blood and input function measurements can translate to errors in $\overline{R}_1^{ext}(t \geq T_2^{inj})$, and hence degrade the results of the signal separation procedure.

B. Signal Extrapolation by Component Analysis

Component analysis methods such as PCA and FADS represent the dynamic PET signal for a tracer as a linear sum of M independent (or pseudo-independent) components $V_m(t)$:

$$R(t) = \sum_{m=1}^{M} \alpha_m V_m(t), \quad (5)$$

where the scalar coefficients $\{\alpha_m\}$ denote the relative weights of each component. The components are usually obtained from empirical population studies, and in general a relatively small number of components can be used to accurately represent the signal. In situations where the coefficients $\{\alpha_m\}$ for tracer 1 can be accurately estimated from the measured data at times $0 \leq t < T_2^{inj}$ (e.g. by fitting eq. (5)), the component representation can be used to extrapolate the signal for $t \geq T_2^{inj}$. Note that this requires that each component have sufficient signal power at $0 \leq t < T_2^{inj}$ that it can be accurately estimated.

The signal extrapolation methods for background subtraction rely upon being able to accurately predict future signals from the measurement at $0 \leq t < T_2^{inj}$. In situations where "late" characteristics of the signal for tracer 1 are important (for example, characterizing a washout phase), background subtraction may not be as preferable unless $T_2^{inj}$ is sufficiently late that the characteristics of tracer 1 are well-defined before administration of the second tracer. This limitation is somewhat diminished for the more advanced model-based signal separation algorithms described below, which use all of the measured timeframes to recover each of the tracer signals.

II. Model-Based Signal Separation

Unlike background subtraction, which treats residual activity from prior injections as a background "contaminant" on the overlapping portion(s) of the scan, model-based signal separation methods treat the entire dataset as a combined measurement and use the full dataset to recover the individual tracer signal components. Recall from equation (1) that the multi-tracer PET signal represents a sum of the individual tracer signal components, model-based signal separation methods assign a kinetic model to each tracer's dynamic signal $R_n(t)$. Again, the kinetic model can be a compartment model, more general kinetic model, component representation, or other model. Furthermore, it is not necessary to use the same model or type of model for each tracer. Associated with each model are a set of unknown parameters which describe the magnitude and kinetics of $R_n(t)$. In some cases one or more parameters may be shared among tracers (e.g. the anatomic parameter $f_B$ with compartment modeling). Model-based signal separation works by simultaneously estimating these parameters for each tracer, giving a modeled signal $\overline{R}_n(t)$ for each tracer, and then using the modeled signals as constraints to recover the separated individual tracer signals. Two methods of model-based signal separation are described in more detail below, model-restricted signal recovery and model-guided signal separation.

A. Model-Restricted Signal Recovery

When the kinetic model for a given tracer is considered to be very accurate, then the recovered signal for that tracer can be exactly constrained by the model. In other words, the recovered signal is restricted to fall within the possible solution space of the model, thus:

Model-Restrictive Signal Separation: $\hat{R}_n(t) = \overline{R}_n(t)$. (7)

In this case, the estimated parameters for the model and the recovered signal are mutually consistent. The parameter estimates are affected by statistical noise in the measurement, but the recovered signal $\hat{R}_n(t)$ "appears" noise free (i.e. is regularized by the model). This method is useful when the desired imaging endpoints are the parameters of the kinetic model themselves. This method may give rise to errors when the models are not accurate, and/or when other endpoints such as static images or SUVs are desired. When a portion of the measured signal contains contributions from only one tracer (e.g., after injection of the first tracer but before injection of the second), the recovered signal for that portion can avoid the restriction and simply be set equal to the measurement (e.g. $\hat{R}_1(0 \leq t < T_2^{inj}) = \tilde{R}_{multi}(t)$).

B. Model-Guided Signal Recovery

Model-guided signal recovery uses modeled kinetic constraints in a less restrictive fashion, such that they minimally act to separate the multi-tracer measurement into single-tracer components. The goal is to separate the measurement (including the noise in the measurement) into recovered single-tracer datasets representative of what would have been obtained by separate, single-tracer imaging without placing additional restrictions on the recovered signals. The recovered signals for each tracer can then be analyzed in any manner desired as with conventional single-tracer imaging.

The modeled signal for each tracer, $\overline{R}_n(t)$, is considered to be an approximate representation of the kinetic behavior of each tracer; however, it is recognized that the kinetic models may contain some deficiencies. While some kinetic constraints from these models are necessary to perform the multi-tracer signal separation, it is not necessary to constrain the recovered signals to exactly match the kinetic models. One way to do this is to use the modeled signal for each tracer to predict the proportion of the total signal due to each tracer, and then distribute the (noisy) measured signal among the individual tracers accordingly:

Model-Guided Signal Separation:

$$\hat{R}_n(t) = \frac{\overline{R}_n(t)}{\sum_{i=1}^{N} \overline{R}_i(t)} \times \tilde{R}_{multi}(t). \quad (8)$$

This process conserves the total magnitude of the measured signal at each time $$\left( \sum_{n=1}^{N} \hat{R}_n(t) = \tilde{R}_{multi}(t) \right)$$

for every t), it distributes the noise in $\tilde{R}_{multi}(t)$ among the tracers, and any errors/inaccuracies in $\overline{R}_n(t)$ have less direct impact upon the results than the prior method. In addition, equation (8) ensures that the recovered signal exactly equals the measured signal in non-overlapping portions of the data (i.e., when the modeled signals $\overline{R}_n(t)$ are zero for all tracers but one). Several variations of equation (8) may be considered that implement the kinetic constraints in somewhat different ways. For example, when non-uniform temporal sampling is used, the constraints can be implemented such that the recovered signal for a slowly-varying tracer can not fluctuate rapidly during the shorter timeframes, whereas that for a faster-varying tracer can be allowed to do so.

Several examples of model-based signal separation are now provided:

C. Model-Based Signal Separation by Compartment Modeling

Consider the case of imaging N tracers by multi-tracer PET. Using a parallel multi-tracer compartment model, the total activity concentration in a PET voxel or ROI can be written:

$$R_{multi}(t) = f_B \sum_{n=1}^{N} B_n(t) + (1 - f_B) \sum_{n=1}^{N} A_n(t; b_n(t), \{k_i\}_n, \lambda_n), \quad (9)$$

where $B_n(t)$ and $A_n(t; b_n(t), \{k_i\}_n, \lambda_n)$ are the activity concentrations in whole-blood and extra-vascular tissue, respectively, for tracer n. Here, $A_n(t)$ is dependent upon that tracer's input function $b_n(t)$, rate parameters, $\{k_i\}_n$, and radioactive decay constant $\lambda_n$. It is assumed in this example that the vascular fraction, $f_B$, is constant throughout the scan (however, it is to be recognized that this condition may not hold for all cases, such as rapid dual-injection rest/stress cardiac imaging where a vasodilator is administered at some point during the scan). It is also assumed that $B_n(t)$ and $b_n(t)$, are known for each tracer (e.g. from blood sampling). The parameters $f_B$ and $\{k_i\}_n$ for every n are the unknowns which can be estimated by fitting the multi-tracer compartment model to the measured data, $\tilde{R}_{multi}(t)$. Let $\hat{f}_B$ and $\{\hat{k}_i\}_n$ be the best-fit parameters. The modeled signal for tracer n is then:

$$\overline{R}_n(t) = \hat{f}_B B_n(t) + (1 - \hat{f}_B) \hat{A}_n(t; b_n(t), \{\hat{k}_i\}_n, \lambda_n). \quad (10)$$

Model-restrictive or model-guided signal separation can then be performed by application of equation (7) or equation (8), respectively. The recovered signal for each tracer, $\hat{R}_n(t)$, can then be processed according to conventional single-tracer analysis methods as described herein or as known to those of ordinary skill in the art.

D. Model-Based Signal Separation by Component Analysis

Considering the same problem as described in the above example and using component-based kinetic models:

$$R_{multi}(t) = \sum_{n=1}^{N} R_n(t) = \sum_{n=1}^{N} \left( \sum_{m=1}^{M_n} \alpha_{m,n} V_{m,n}(t) \right), \quad (11)$$

where $\alpha_{m,n}$ and $V_{m,n}(t)$ are the $m^{th}$ coefficients and components for tracer n, respectively, and $M_n$ is the number of components for tracer n. The components $V_{m,n}(t)$ are assumed known from prior component analysis, and unknowns are $\alpha_{m,n}$. Fitting equation (11) to the measured data, $\tilde{R}_{multi}(t)$, to obtain best-fit parameters $\hat{\alpha}_{m,n}$, the signal for each tracer is modeled as:

$$\overline{R}_n(t) = \sum_{m=1}^{M_n} \hat{\alpha}_{m,n} V_{m,n}(t). \quad (12)$$

Again, model-restrictive or model-guided signal separation is performed through application of equation (7) or equation (8), respectively.

E. Model-Based Signal Separation with Mixed Kinetic Models

The signal separation algorithms can also be applied using different kinetic models for each tracer. For example, one or more tracers may be characterized by compartment models, and one or more others may be characterized by component analysis. The modeled signal $\overline{R}_n(t)$ follows either equation (10) or equation (12) according to the kinetic model for tracer n, and the signal separation proceeds as above.

Multi-Tracer Imaging Endpoints

For conventional single-tracer PET imaging, dynamic imaging is only performed when some form of kinetic analysis is needed, e.g. quantification of kinetic rate parameters or characterization of retention times. While dynamic imaging is common in the research setting, the majority of clinical PET scans are performed in static mode, with static images and imaging measures (e.g. SUVs) being the most common endpoints. Multi-tracer PET signal separation techniques require that dynamic imaging be performed in order to utilize kinetic constraints to perform the signal separation. This differs from single-tracer imaging in that dynamic mode is necessitated by the need for multi-tracer signal separation, not by the need for kinetic analysis endpoints. While the recovered signals for each individual tracer contain kinetic information and can be analyzed as such, static images and endpoints may be desired for many tracers and potential clinical applications. This does not pose a problem, as $\hat{R}_n(t)$ can be summed or integrated over time to produce corresponding static measurements. Indeed, since some degree of kinetic information is lost in the overlapping multi-tracer portions of the scan, certain kinetic measures may not be well recovered by the signal separation techniques whereas corresponding static measures may still be recovered accurately. Since the accuracy of each possible imaging endpoint depends on the tracers present, injection sequence and timing, quality of the data, and performance of the signal separation algorithm, care should be taken to identify the target endpoints in advance and design the multi-tracer imaging protocol accordingly. Significant work may be required to develop multi-tracer imaging protocols for specific tracer combinations and clinical applications.

The signal separation algorithms presented herein are described for generic imaging signals $R(t)$, where the signal can represent several types of data including dynamic projection data, a dynamic series of reconstructed image time-frames, and/or time-activity curves computed for individual voxels or larger regions-of-interest. In the same manner that single-tracer kinetic analysis methods have been studied for each of these data types, multi-tracer signal separation can be applied to each as well. A series of examples of particular imaging endpoints are present below, contemplating what multi-tracer imaging signals and data types could be used for achieving the desired endpoint.

Static Image A static image in PET displays the radioactivity (or radioactivity concentration) in each voxel averaged (or integrated) over some time $t_1$ to $t_2$. Under the condition that the actual radioactivity distribution is fixed or at equilibrium (disregarding radioactive decay), which is a common assumption or approximation for many imaging scenarios, the static image represents the "final" distribution of the tracer. To obtain a static image of tracer n from multi-tracer PET, signal separation considers each voxel of the image. Typically, a multi-tracer signal $R_{multi}(t)$ would be identified as the time-activity curve for each voxel (though kinetic analysis methods which operate on clusters of voxels or the four-dimensional (4D) image as a whole might also be considered). The recovered signal $\hat{R}_n(t)$ is also a time-activity curve, which can be integrated from $t_1$ to $t_2$ to produce the recovered voxel value. Repeating this process for every image voxel and collecting the results, the recovered static image of tracer n is formed.

Standardized Uptake Value (SUV) A common imaging endpoint for oncologic PET is the SUV of a tumor, representing the uptake of the tracer in a tumor ROI normalized by the injected dose and body mass (or body surface area). Again, this is a static imaging measure computed for a "static" image acquired from times $t_1$ to $t_2$. One approach to measuring an SUV for tracer n in multi-tracer PET would be to first create the static image as described above, and then compute the SUV from the static image. When the static image is not needed, the SUV could also be computed more directly by identifying the multi-tracer signal $R_{multi}(t)$ as the time-activity curve for the ROI under consideration. Signal separation is performed, yielding the recovered time-activity curve $\hat{R}_n(t)$ for tracer n, which is then integrated from $t_1$ to $t_2$ and the SUV calculation is performed.

Kinetic Rate Parameter or Macroparameter Dynamic PET imaging with compartment modeling can be used to quantify kinetic rate parameters or macroparameters describing tracer uptake, retention, or washout. Common examples include quantification of blood flow as the wash-in rate constant $k_1$ for tracers such as $^{15}$O-water, $^{13}$N-ammonia, or $^{72}$Rubidium; or quantification of the metabolic rate of glucose metabolism using the net uptake $k_1k_3/(k_2+k_3)$ of $^{18}$F-fluorodeoxyglucose. The kinetic parameters or macroparameters are generally estimated on a regional or ROI basis. For multi-tracer PET, then, the multi-tracer signal $R_{multi}(t)$ can be identified as the time-activity curve for the ROI under consideration. Two approaches can be taken to estimate the endpoint parameter(s). Model-restricted signal separation can be applied, using the appropriate compartment model for tracer n such that the desired kinetic parameter is estimated directly from the fitting step of the signal separation algorithm. In fact, if the kinetic parameter is the only endpoint of interest, signal separation need not be completed as the parameter is already estimated by the fitting step. While this approach directly estimates the parameter of interest, it is also more sensitive to any deficiencies in the kinetic models—both for tracer n and for errors propagating from the other tracers present. As another approach, Model-guided signal separation can be performed to separate $R_{multi}(t)$ and recover $\hat{R}_n(t)$, where it is noted that the kinetic model used for this separation may be the same as or differ from the one used to compute the final parameter endpoint. The recovered signal is then analyzed using single-tracer methods to obtain the final parameter estimate. Error propagation differs for Model-guided vs. model-restricted signal separation, and determination of the more efficacious algorithm for estimating a kinetic parameter for a particular tracer and multi-tracer protocol is a matter for further investigation.

Parametric Images Parametric images display kinetic parameters on a voxel-by-voxel basis. Multi-tracer signals $R_{multi}(t)$ are typically identified for each individual voxel, though kinetic analysis methods which operate on clusters of voxels or the 4D image as a whole might also be considered. The same methods as described for computing a kinetic parameter for a single region can be applied for each of the voxels, with the results collected to form the desired parametric image. Since different body tissues may have different kinetics for a given tracer, care should be taken to ensure that appropriate kinetic constraints are used for each voxel.

EXAMPLES AND EVALUATION METHODS

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for.

I. First Example

Figure 2A:
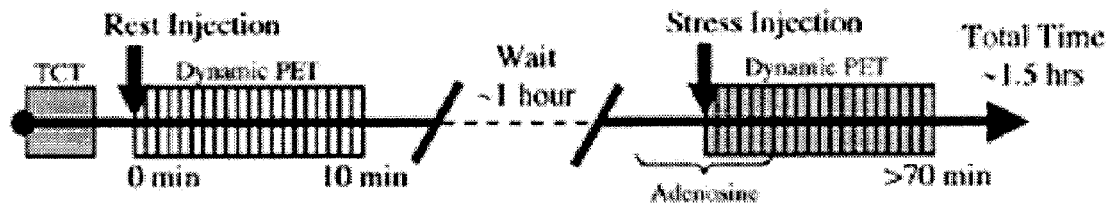
FIG. 2A illustrates conventional methods for measuring cardiac blood flow at rest and during stress with a tracer such as, for example, $^{13}$N-ammonia PET requiring a waiting period of about an hour between scans to allow for radioactive decay.
Figure 2B:
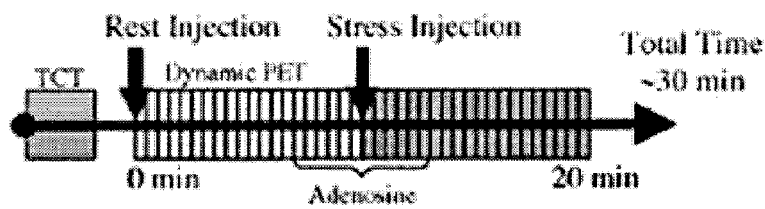
FIG. 2B illustrates an embodiment of a rapid dual-injection, single-scan imaging process.

FIG. 2A illustrates conventional methods for measuring cardiac blood flow at rest and during stress with a tracer such as, for example, $^{13}$N-ammonia PET requiring a waiting period of about an hour between scans to allow for radioactive decay. An embodiment of a rapid dual-injection, single-scan imaging process is illustrated in FIG. 2B. In FIG. 2B, after the patient is positioned in the scanner and a transmission scan has been acquired for attenuation correction, dynamic PET is performed continuously while injections of a tracer such as, for example, $^{13}$N-ammonia are administered at the scan start during rest and a short time later (e.g., 10 minutes) during adenosine stress. This rapid dual-injection approach reduces the overall procedure time significantly compared to conventional single-injection methods. Potential advantages of embodiments of the rapid dual-tracer process include increased scanner throughput and utilization, improved co-registration of rest and stress data, reduced motion artifact, reduced transmission scan radiation exposure and improved patient comfort and convenience. Another advantage is that if the two doses tracer are the same (for example, the first injection and the second injections are $^{13}$N-ammonia), the injections may be obtained from a single cyclotron run and split for the rapid sequential injections.

Quantification of myocardial perfusion using rapid dual-injection single-scan PET presents a technical challenge. While rest measurements are unaffected by the dual-injection approach, stress measurements can be complicated by significant interference from the rest injection. The background activity from the rest injection remaining in the myocardium during the stress measurement can be typically about 10-20% of the total activity and can be even higher in cases with a stress defect. Processes such as tracer kinetics, metabolic trapping and radioactive decay all need to be carefully considered when applying a kinetic model for quantification of dual-injection data.

One challenge of evaluating the rapid dual-injection approach in humans is the need for a standard for comparison purposes. One option would be to acquire separate rest, stress and dual-injection scans in each subject; however, previous work has shown up to 10-15% variability in global blood flow estimates in repeated scans (Nagamachi et al 1996), and such an approach would require twice the radiation exposure and adenosine effects for each participant. Therefore, a process is described herein where separate cardiac rest and stress scans are acquired, which provide a standard for each measurement, and the data combined to emulate a rapid dual-injection acquisition. From this process, methods of evaluating rapid dual-injection single-scan $^{13}$N-ammonia PET are derived for the quantification of rest and stress myocardial blood flows.

In the exemplary process of FIG. 2B, a 20 minute dynamic emission scan protocol with tracer injections staggered about 10 min apart is employed. In this instance, all tracer injections are comprised of $^{13}$N-ammonia and the subjects are human subjects, though other tracers and subjects are contemplated within the scope of the invention. To begin the process, and to verify the derived results, separate rest and stress scans can be acquired, providing a standard for each measurement, and the data combined to emulate a rapid dual-injection. Various methods, including background subtraction and combined modeling, as previously described herein, can be applied for quantification of regional myocardial blood flows from dual-injection data. Quantitative results from the rapid dual-injection single-scan approach can be verified against results from conventional separate single-injection rest and stress scans using linear regression and Bland-Altman analysis (Bland and Altman 1986).

A. Data Acquisition and Processing Methods

Data acquisition. PET scans can be performed using, for example, an Advance™ PET scanner (GE Medical Systems, Waukesha, Wis.) operated in 2D mode, though other PET scanners are contemplated within the scope of this invention. Human subjects, when used, were positioned with arms down and a strap was placed across the chest to immobilize the subject and minimize movement artifacts. Transmission scans ($^{68}$Ge rod source) were acquired to position the heart in the field of view (2 min) and for attenuation correction (10 min). In one exemplary process at the start of each emission scan, 21.5±4.0 mCi $^{13}$N-ammonia was administered intravenously over about 20-30 seconds followed by a saline flush. Scans performed during stress were started at the midpoint of a 6 minute adenosine infusion (0.14 mg kg$^{-1}$ min$^{-1}$) while vital signs including pulse rate, blood pressure and oxygen saturation were assessed by a physician using standard monitoring equipment.

Dynamic PET data were acquired with a waiting period of about 50-71 min between rest and stress emission scans. Imaging protocols were designed to allow rest and stress components to be added to emulate rapid dual-injection data as further described herein. Rest and stress emission scan data were acquired separately using the following temporal sampling schedule for the first 10 minutes: (12×5 s, 6×10 s, 6×30 s and 5×1 min). For rest scans, this schedule was repeated for another 10 minutes for a total emission scan duration of about 20 minutes. This provided equal duration stress timeframes that could be shifted in time and added to the rest timeframes in order to mimic a rapid dual-injection acquisition while retaining standard single-injection emission scan sequences. In addition, an actual rapid dual-injection PET scan was acquired in one human subject; in that case, one injection of $^{13}$N-ammonia was given at the scan start during rest, adenosine was infused from 7 to 13 min, and a second tracer injection was given at 10 min during stress.

Data processing. According to one embodiment, images were reconstructed using filtered back-projection with a Hanning window cutoff at 1.56 cycles cm$^{-1}$. The 128×128 image matrices had 4.3 mm voxels and a slice thickness of 4.25 mm. Data were pre-corrected for attenuation, scatter and randoms prior to reconstruction, but not for radioactive decay because it was included in the kinetic modeling equations. A reference image for each scan was created by summing up timeframes with steady uptake of tracer in the myocardium and used as a guide for reorienting to cardiac short-axis (SA) images. The SA images for all rest and stress timeframes in each subject were co-registered using a template showing the endocardial and epicardial boundaries. Based on visual comparison of an average mid-ventricular slice from each timeframe, the entire SA image volume was shifted manually to align with the template in the plane perpendicular to the SA of the heart. Co-registration was not performed in timeframes where myocardium and blood pool were indistinguishable.

Myocardial regions were selected based on a 17-segment model of the American Society of Nuclear Cardiology (Schelbert et al. 2003), known to those of ordinary skill in the art. On each slice of a reference image, endocardial and epicardial boundaries were drawn and the angle of insertion of the right ventricle into the septum was selected as a landmark for division into sectors. The myocardium was divided into one apical region, four sectors in the apical mid-ventricle, six sectors in the basal mid-ventricle and six sectors in the base of the heart. Blood pool regions were drawn manually in each subject with size restricted to limit partial volume effect and spillover of activity from the myocardium. In each subject, the same regions were applied to all co-registered rest and stress timeframes. Time-activity curves were computed as the average activity concentration in the region at the midpoint of each timeframe, and activity was set to zero prior to the initial bolus entering the blood pool.

Emulation of rapid dual-injection data. Separate single-injection rest and stress scans were acquired as standards for comparisons, and the data from these scans were also combined to emulate rapid dual-injection imaging. This approach provided dual-injection data where the components of activity from the rest and stress injections were known exactly. Regional myocardial blood flow estimates were computed from the dual-injection data and evaluated versus estimates obtained from the separate rest and stress components. This approach eliminated factors that usually contribute to differences in blood flow measures in repeated scans, including differences in noise realizations, region-of-interest selection, patient movement and physiological changes. Interference due to signal overlap and the methods used to quantify blood flow were the only sources of differences between the rapid dual-injection results and separate single-injection standards. A possible limitation of this approach is that the component of activity from the rest injection was not affected by adenosine, which would be infused from 7 to 13 min during an actual rapid dual-injection scan and could affect the tail end of the rest component (see FIG. 2B).

Rapid dual-injection dynamic PET data were emulated by combining the rest and stress time-activity curves for each myocardial region after the data were reconstructed and images co-registered. Rest and stress data were acquired separately using the dynamic sampling schedules as previously described herein. The stress time-activity curves were shifted in time and added to the rest curves to mimic a 20 minute rapid dual-injection acquisition with a 10 minute delay between injections. The 10 minute delay was chosen to provide a good tradeoff between imaging time and quantitative accuracy based on preliminary simulations and previous work with a similar tracer (Rust and Kadrmas 2006), but other delay periods are contemplated within the scope of this invention. The delay provides enough time to obtain estimates of rest blood flow without interference from the stress injection and allows tracer kinetics from the rest injection to stabilize before the start of adenosine infusion.

B. Quantification Methods for Rapid Dual-Injection Data

Figure 3:
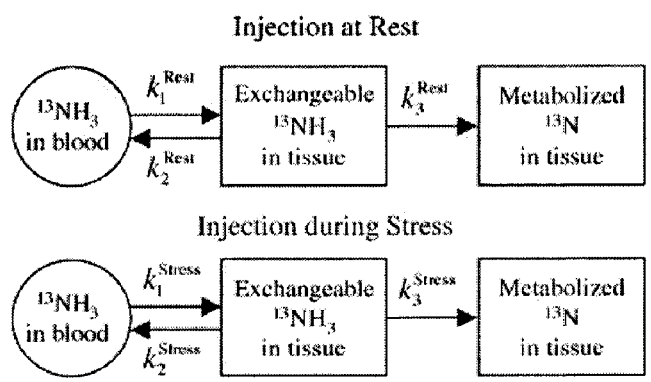
FIG. 3 illustrates exemplary compartment models for $^{13}$N-ammonia PET at rest (top) and stress (bottom), as known to those of ordinary skill in the art, which can be used to quantify blood flow from rapid dual-injection PET data.

Compartment model. Quantitative estimates of myocardial blood flow were obtained by fitting the exemplary compartment model shown in FIG. 3 to the dynamic PET data (Hutchins et al 1990, Choi et al 1999). FIG. 3 illustrates exemplary compartment models for $^{13}$N-ammonia PET at rest (top) and stress (bottom), as known to those of ordinary skill in the art, which can be used to quantify blood flow from rapid dual-injection PET data. FIG. 3 specifically illustrates a two tissue-compartment model with irreversible trapping that was applied for rest and stress with two different sets of rate parameters. Separate blood input functions for the rest and stress injections were obtained from the dual-injection data, and the effects of radioactive decay were included in the modeling equations (below). Using this model, the $^{13}$N activity concentration in a myocardial region-of-interest, R(t), can be written using equation (4), above, where in this instance $f_B$ is the total fractional blood volume, B(t) is the $^{13}$N activity concentration in the whole blood and A(t) is the $^{13}$N activity concentration in the myocardial tissue. For conventional separate single-injection rest and stress scans, A(t) can be modeled including the effects of radioactive decay as $$A(t) = \left[\frac{k_1 k_3}{k_2 k_3} e^{-\lambda t} + \frac{k_1 k_2}{k_2 + k_3} e^{-(k_2 + k_3 + \lambda)t}\right] \otimes b(t) \quad (13)$$

where {$k_i$} are kinetic rate constants, $\lambda$ is the radioactive decay constant, $\otimes$ is the convolution operator and b(t) is the metabolite-corrected blood input function. The input function, b(t), is the fraction of unmetabolized and freely exchangeable $^{13}$N-ammonia available in the whole blood, B(t), at time t. In this study, metabolite correction was performed based on average values previously reported in the literature (Rosenspire et al 1990, Bormans et al 1995), and known to those of ordinary skill. A modified Levenberg-Marquardt algorithm for chi-squared minimization was used to find the best fit parameters (Press et al. 1992), also known to those of ordinary skill in the art, where the data were weighted by the timeframe durations in order to compensate for non-uniform temporal sampling. The kinetic rate constants were limited to non-negative values, $k_2$ was constrained to be less than or equal to $k_1$ and $f_B$ was limited to range from 0 to 1. Using this model, $k_1$ provided a quantitative estimate of myocardial perfusion with units of ml min$^{-1}$g$^{-1}$.

For the separate single-injection scans only the first 10 min of data were used and fit to the model, and for the rapid dual-injection scans the full 20 min of dynamic data were used as described in the following sections. Rapid dual-injection data could be represented using an equation of the same general form as equation (4); however, kinetic parameters would not be constant due to the infusion of adenosine during the scan. Development of an advanced kinetic model that exactly matched actual rapid dual-injection data including transient changes in blood flow due to adenosine infusion was not attempted and would not be applicable to the emulated dual-injection data used to obtain the referenced standard. The basic model applied in this work considers the dual-injection data to be the sum of time-activity curve components from rest and stress injections, where each component is represented using the model described above. With this limitation, background subtraction and combined modeling were applied to test the rapid dual-injection approach. Separate rest and stress whole blood curves and metabolite-corrected input functions were needed to apply these methods and were obtained from the dual-injection data as also described below.

Figure 4:
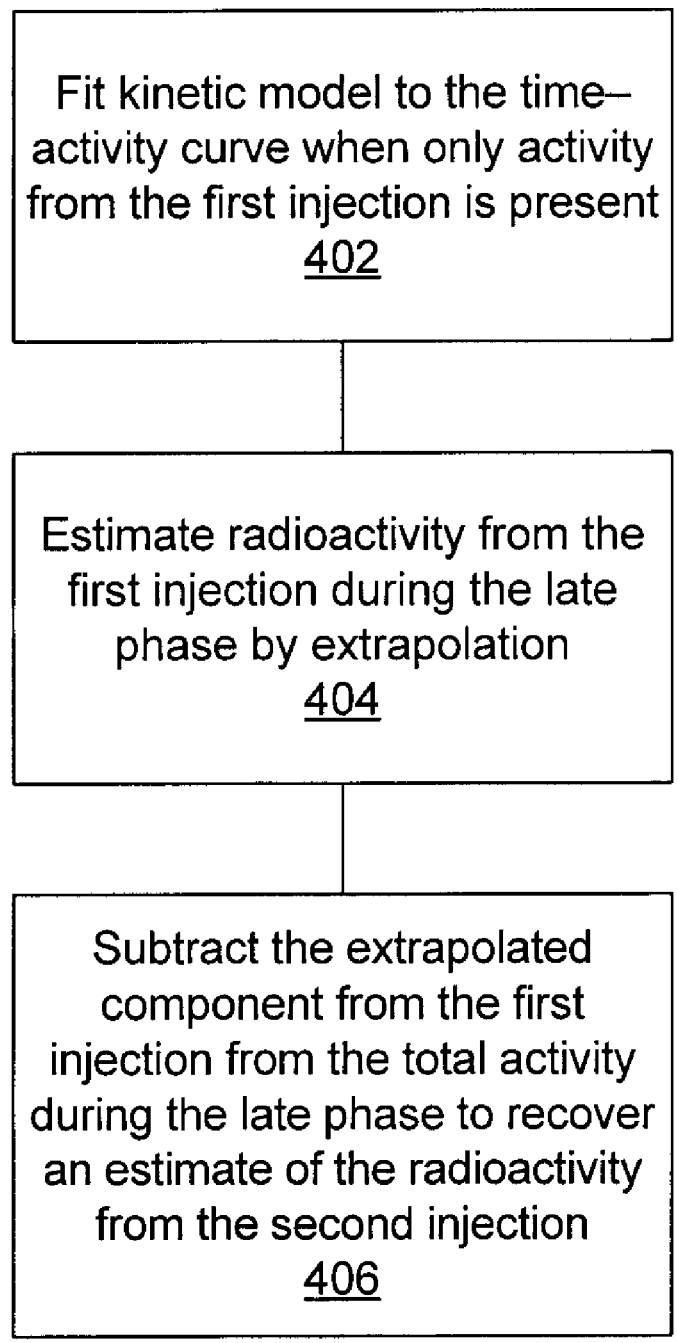
FIG. 4 is an exemplary flowchart for a process of quantification of rapid dual-injection data by treating the data analysis according to a background subtraction problem whereby components from each injection are separated in several stages.

Background subtraction method. One method for quantification of rapid dual-injection data is to treat the stress data analysis as a background subtraction problem, as previously described herein. This method considers the data as the sum of activity from two injections. The components from each injection are separated in several stages as shown in the exemplary flowchart of FIG. 4. At step 402, a kinetic model is fit to the early phase of the time-activity curve when only activity from the first injection is present. At step 404, an estimate of the radioactivity from the first injection during the late phase is obtained by extrapolation. At step 406, the extrapolated component from the first injection is subtracted from the total activity during the late phase to recover an estimate of the radioactivity from the second injection. Once the time-activity curves for each injection are separated, standard quantification methods can be applied to each component.

In this instance, the conventional model described above was fit to the first 10 min of dual-injection data to estimate kinetic parameters during the rest part of the scan. As a result, the rest blood flow estimates were identical to what would be obtained from a separate single-injection rest scan. For the background subtraction method, the rest kinetic parameters were used to extrapolate the $^{13}$N activity concentration in the heart for the stress portion of the scan over the period from 10 to 20 min:

$$R_{Ext.}^{Rest}(t>10\text{ min})=f_B B^{Rest}(t)+(1-f_B)A^{Rest}(t) \quad (14)$$

where $B^{Rest}(t)$ is the rest whole blood curve obtained from the dual-injection data as described below and $A^{Rest}(t)$ is the extrapolated activity concentration in the tissue from the rest injection. Stress kinetic parameters were estimated by fitting the recovered stress curve, which was obtained by subtracting the extrapolated rest curve from the dual-injection data:

$$[R^{Dual}(t)-R_{Ext.}^{Rest}(t)]=f_B B^{Stress}(t)+(1-f_B)A^{Stress}(t) \quad (15)$$

where $f_B$ and $\{k_i^{Stress}\}$ are estimated by the fitting procedure. The separate stress whole blood curve, $B^{Stress}(t)$, and input function were obtained from the dual-injection data as described below.

Combined modeling. The application of a combined model, which can account for the activity from both injections and the two different physiologic states, was also tested in this exemplary work. Using this method, kinetic parameters for rest and stress were simultaneously estimated by performing a fit to all of the rapid dual-injection data.

Described herein, a combined model applicable to the emulated data was tested in order to determine whether or not all the rest and stress parameters could be simultaneously estimated from the rapid dual-injection data. The total $^{13}$N activity concentration in a myocardial region, $R^{Dual}(t)$, can be written as the sum of time-activity curves for rest and stress injections:

$$R^{Dual}(t)=[f_B^{Rest}B^{Rest}(t)+(1-f_B^{Rest})A^{Rest}(t)]+[f_B^{Stress}B^{Stress}(t)+(1-f_B^{Stress})A^{Stress}(t)] \quad (16)$$

where $f_B^{Rest}$, $\{k_i^{Rest}\}$, $f_B^{Stress}$ and $\{k_i^{Stress}\}$ are simultaneously estimated by the fitting procedure.

This model configuration was designed to match the emulated dual-injection data according to the current study, which were formed by combining separate rest and stress scans. The combined model was fitted to all 20 minutes of dual-injection data, and a total of eight parameters were recovered by the fitting procedure. Fits to the dual-injection data were performed using the same algorithm, parameter constraints, initial values and number of iterations as used in the fits to separate single-injection data. Several different weighting strategies were investigated in this work, all of which provided similar results. This combined model was also used to fit the data from the actual rapid dual-injection scan acquired in one person as an example.

Blood curve separation. Separate rest and stress blood curves need to be recovered from the dual-injection data in order to quantify blood flow using the methods described above. These curves are not readily available from the images because there is a small amount of residual $^{13}$N activity from the rest injection in the blood pool region that overlaps with the activity from the stress injection during the period from 10 to 20 min (see FIG. 5).

However, previous studies of $^{13}$N-ammonia metabolism in the blood have shown that a large fraction of the total residual $^{13}$N activity in the blood is metabolically trapped within 10 min post-injection (Rosenspire et al 1990, Bormans et al 1995). Twenty minutes of separately acquired rest data were available in this study and used to test several models for extrapolating the rest whole blood curve for dual-injection data. Very little difference was observed between the various models, and it was found that the $^{13}$N activity concentration in whole blood from the rest injection, $B^{Rest}(t)$, can be modeled as a constant times radioactive decay during the period from 10 to 20 min:

$$B^{Rest}(t)=\alpha e^{-\lambda t}, \quad (17)$$

where $\alpha$ is unknown and $\lambda$ is the radioactive decay constant. For dual-injection data, $\alpha$ was obtained by performing a least-squares fit to the blood pool time-activity curve using timeframes from 5 to 10 min post-injection. The residual $^{13}$N activity in the whole blood from the rest injection was then extrapolated over the period from 10 to 20 min and subtracted from the dual-injection blood curve to obtain the stress whole blood curve, $B^{Stress}(t)$. Input functions for each component were obtained by correcting the whole blood curves for $^{13}$N-labelled metabolites starting from the time of each injection and based on average values reported in the literature (Rosenspire et al 1990, Bormans et al 1995).

The measured rest and stress blood curves were available in this study because the dual-injection data were emulated by adding separately acquired rest and stress components, and the effects of the blood curve separation procedure were assessed using these measured curves. The mean difference (±standard deviation) between blood flow estimates obtained from dual-injection data using the separation procedure compared to using the measured rest and stress blood curves was 0.016±0.023 ml min$^{-1}$ g$^{-1}$.

C. Results

Dynamic PET imaging data were successfully obtained for human subjects, one subject having a left-ventricle assist device (LVAD), providing a wide range of blood flows. Regional myocardial blood flow estimates were computed in 17 regions per subject (n=102), with one region in the LVAD patient where the fitting routine failed to provide reasonable results. The mean±standard deviation of myocardial blood flow estimates over 101 myocardial regions based on the separate single-injection results in these subjects was 0.70±0.36 ml min-1 g$^{-1}$ at rest and 2.25±1.70 ml min1 g$^1$ during stress. Four of the subjects provided blood flow values in a normal range (rest: 0.91±0.23 ml min$^{-1}$ g$^{-1}$, stress: 3.20±1.24 ml min$^{-1}$ g$^{-1}$), and the subject with a LVAD provided two datasets with abnormally low flows at rest (0.28±0.13 ml min$^{-1}$ g$^{-1}$) and during stress (0.31±0.11 ml min$^{-1}$ g$^{-1}$).

Single region example. Rapid dual-injection data for a typical region are shown in FIG. 5, along with a fitted curve obtained using the combined modeling method. FIG. 5 is a typical example of emulated rapid dual-injection data as used in this study. Time-activity curves (which have not been decay corrected) are shown for the blood pool and one myocardial region, along with a fitted curve obtained using the combined modeling method. Increases in the activity concentration are clearly distinguishable following the rest and stress injections, and the activity stabilizes within a few minutes after each injection. The rest and stress input functions were recovered from the whole blood curve as described herein.

Quantitative results for this case are provided in Table 1, where the uncertainties are estimates of standard deviations obtained from the formal covariance matrix of the fit on the assumption of normally distributed errors (Press et al 1992).

TABLE 1

| Parameter | Separate Single-Injection | Background Subtraction | Combined Modeling |
|---|---|---|---|
| $k_1^{Rest}$ | 0.92 ± 0.05 | 0.92 ± 0.05 | 0.93 ± 0.05 |
| $k_2^{Rest}$ | 0.13 ± 0.04 | 0.13 ± 0.04 | 0.14 ± 0.04 |
| $k_3^{Rest}$ | 0.08 ± 0.07 | 0.08 ± 0.07 | 0.11 ± 0.06 |
| $k_4^{Rest}$ | 0.47 ± 0.02 | 0.47 ± 0.02 | 0.47 ± 0.02 |
| $k_1^{Stress}$ | 3.33 ± 0.27 | 3.50 ± 0.32 | 3.44 ± 0.32 |
| $k_2^{Stress}$ | 0.69 ± 0.12 | 0.80 ± 0.17 | 0.79 ± 0.17 |
| $k_3^{Stress}$ | 0.20 ± 0.03 | 0.24 ± 0.04 | 0.24 ± 0.04 |
| $f_B^{Stress}$ | 0.58 ± 0.04 | 0.56 ± 0.05 | 0.55 ± 0.04 |

In the first 1-2 min following each injection, there was a distinct increase in the dual-injection time-activity curve. This increase included a sharp peak arising from the blood component ($f_B \approx 0.5$) and an elevated plateau due to $^{13}N$ uptake by the myocardial tissue. By 10 min, the activity from the rest injection was mostly stable except for radioactive decay, and the additional uptake from the stress injection was clearly distinguishable. The results in Table 1 indicated that the rapid dual-injection approach has only a small effect on blood flow quantification. Note that rest parameter estimates obtained from dual-injection data using the background subtraction method are identical to separate single-injection estimates because both were obtained using only the first 10 minutes of data, and hence were not affected by using the rapid dual-injection protocol. For the case shown in FIG. 5, the stress myocardial blood flow (MBF) estimate from background subtraction was slightly higher than the single-injection value, differing by about 5%. Using the combined modeling method, rest and stress parameters were recovered simultaneously by fitting all 20 minutes of dual-injection data. Rest and stress MBF estimates from combined modeling were both within about 4% of the separate single-injection estimates for this region. As shown in FIG. 5, the fitted curve from combined modeling closely matched the dual-injection data.

Rapid dual-injection versus separate single-injection method. The rapid dual-injection approach provided estimates of myocardial blood flow both for rest and stress very similar to the conventional separate single-injection standards. Results are first presented for the background subtraction method of recovering rest and stress MBF values from the dual-injection data, and results for the more involved combined modeling method are present further herein. Recall that for background subtraction, rest parameter estimates were obtained using the first 10 minutes of data and were identical to those obtained from separate single-injection data. An estimate of the rest activity was then removed from the dual-injection data to recover the stress component. Background subtraction recovered stress blood flow values from dual-injection data very similar to the separate single-injection results over the entire range of values.

FIG. 6 provides a direct comparison of the stress MBF estimates for an embodiment of the present invention (the background subtraction method) versus separate single-injection results for each myocardial region. Background subtraction and the standard single-injection approach provided similar values in all cases, and regions with abnormally low flow were clearly delineated from high flow regions by both methods. Regression analysis was performed to compare MBF estimates from background subtraction versus the standards. As shown by the equation represented in FIG. 6, a strong correlation was observed (r=0.998, slope=1.025 and intercept=0.023). Overall, these results suggest that the rapid dual-injection approach can provide blood flow estimates very similar to conventional separate single-injection rest and stress scans.

Simultaneous rest and stress quantification by combined modeling. In investigating the combined modeling method rest and stress parameters for each myocardial region were recovered by fitting the combined model to 20 min of dual-injection data. Rest and stress MBF estimates from combined modeling were very similar to the separate single-injection comparison standards. FIGS. 7A and 7B compare rest (A) and stress (B) blood flow estimates obtained from rapid dual-injection data according to an embodiment of the present invention using combined modeling versus the separate single-injection standards. The small differences in values obtained from these two methods are examined more closely in FIGS. 8A and 8B.

Rest results. FIGS. 7A and 8A demonstrate that fitting the combined model to the dual-injection data provided rest perfusion estimates very similar to the single-injection standards. Although rest estimates identical to the conventional (single-injection) values could have been obtained by performing a separate fit to the first 10 min of data, the combined modeling method provided nearly identical results in a single step. As shown in FIG. 7A, the correlation between rest MBF estimates from combined modeling versus standard single-injection values is very strong (r>0.999). In FIG. 8A, the differences between rest MBF estimates from combined modeling and standard values for each region are plotted versus the average value from the two methods. This Bland-Altman plot shows that the differences between the two methods were consistently small across the entire range of resting blood flow values in this study. These results show that simultaneous estimation of rest and stress parameters does not have a significant effect on rest results.

Stress results. FIGS. 7B and 8B show that combined modeling provided very similar stress blood flow estimates as compared to the separate single-injection method. Combined modeling also provided similar performance as compared to the background subtraction method. FIG. 7B directly compares stress MBF estimates from the combined modeling method versus single-injection standards for each region. As shown on the plot, the correlation between MBF estimates from combined modeling versus the standards is very strong (r=0.998, slope=1.016, intercept=0.022). Strong correlations versus single-injection results were also observed for $f_B$ (r=0.990) and $k_2$ (r=0.996), with somewhat greater variability for $k_3$ estimates (r=0.953).

The Bland-Altman plot in FIG. 8B allows closer examination of the small differences between stress MBF estimates from combined modeling and the separate single-injection method for each region. Low flow regions were clearly delineated from high flow regions in these data using the rapid dual-injection approach. The mean±standard deviation of the MBF differences was 0.06±0.11 ml min$^{-1}$ g$^{-1}$, and these differences are small relative to the magnitude of clinically significant flow variations. By comparison, the background subtraction method resulted in a slightly higher mean difference versus single-injection values, 0.08±0.12 ml min$^{-1}$ g$^{-1}$. Based on the separate single-injection values, the rapid dual-injection approach tended to slightly overestimate stress MBF (approximately 3%) at normal to high blood flows. This subtle effect may be due to the weights used to perform the fits or because the noise in the reconstructed images is not exactly Gaussian.

In some embodiments, the combined modeling method can also be applied on a voxel-by-voxel basis to recover separate rest and stress images. Using the results of the fit, the relative fraction of activity from the rest and stress injections in each timeframe can be predicted. These data can then be used to separate dual-injection data into rest and stress components. This procedure was applied to the dynamic images, and the results were summed from 5 to 10 min to produce static images. FIG. 9 shows a conventional short-axis stress image, the dual-injection image containing both rest and stress components, and the stress image recovered according to an embodiment of the present invention. The recovered image closely matched the single-injection image, as shown by the profiles in the figure. In the top row of FIG. 9, and from, left to right shows a conventional single-injection stress image, a rapid dual-injection image with activity from both rest and stress, and a recovered stress image. The bottom row of FIG. 9 shows profiles demonstrating that the recovered stress image closely matched the single-injection standard. Stress images were recovered by performing combined modeling fits on a voxel-by-voxel basis and using the fit results to estimate the fraction of activity from the rest and stress injections in each timeframe.

Figure 10:
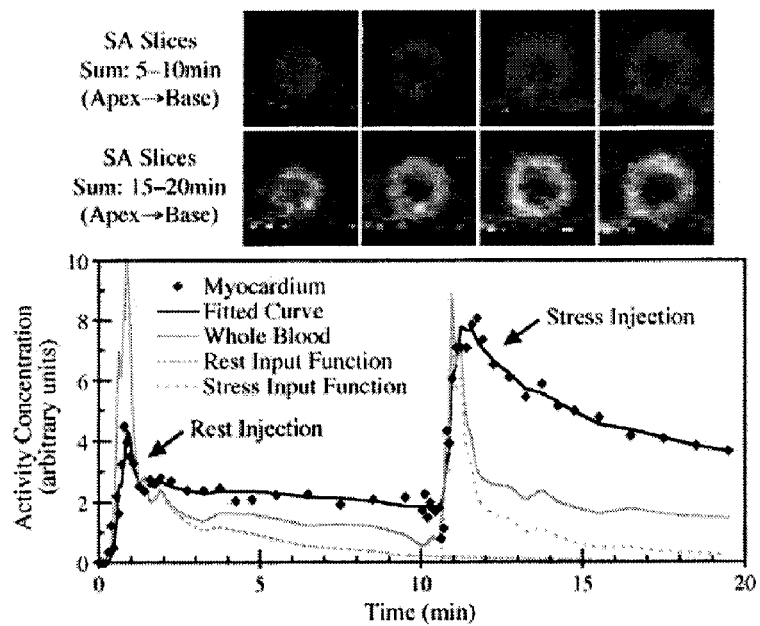
FIG. 10 illustrates short-axis images of the myocardium and time-activity curves for the blood pool and a typical region.

Actual rapid dual-injection scan. An actual rapid dual-injection scan was acquired in one subject in order to demonstrate the feasibility of this approach and to provide an example dataset. Short-axis images of the myocardium and time-activity curves for the blood pool and a typical region are shown in FIG. 10. A 20 min dynamic emission scan was acquired with 18.9 mCi of $^{13}$N-ammonia injected at the scan start during rest, adenosine infused from 7 to 13 min and 18.7 mCi of $^{13}$N-ammonia injected at 10 min during stress. Notably, both injected doses of $^{13}$N-ammonia were obtained from a single cyclotron run. Images were reconstructed and processed using methods similar to those described in regards to data processing, above. Regional myocardial blood flows were quantified using the combined modeling method and the bloodcurve separation procedure as each are described above. As shown in FIG. 10, images were obtained by summing timeframes from 5 to 10 min at rest and by summing timeframes from 15 to 20 min at stress. The mean±standard deviations of MBF estimates over the 17 myocardial regions in this subject were 0.69±0.10 ml min-1 g$^{-1}$ at rest and 2.63±0.51 ml min-1 g$^{-1}$ during stress, and perfusion flow reserves (stress/rest) were 3.96±1.06. Qualitatively, the data for this subject appeared very similar to the emulated dual-injection data used in this study, and the activity from the rest injection was not significantly affected by adenosine.

II. Second Example

Figure 11:
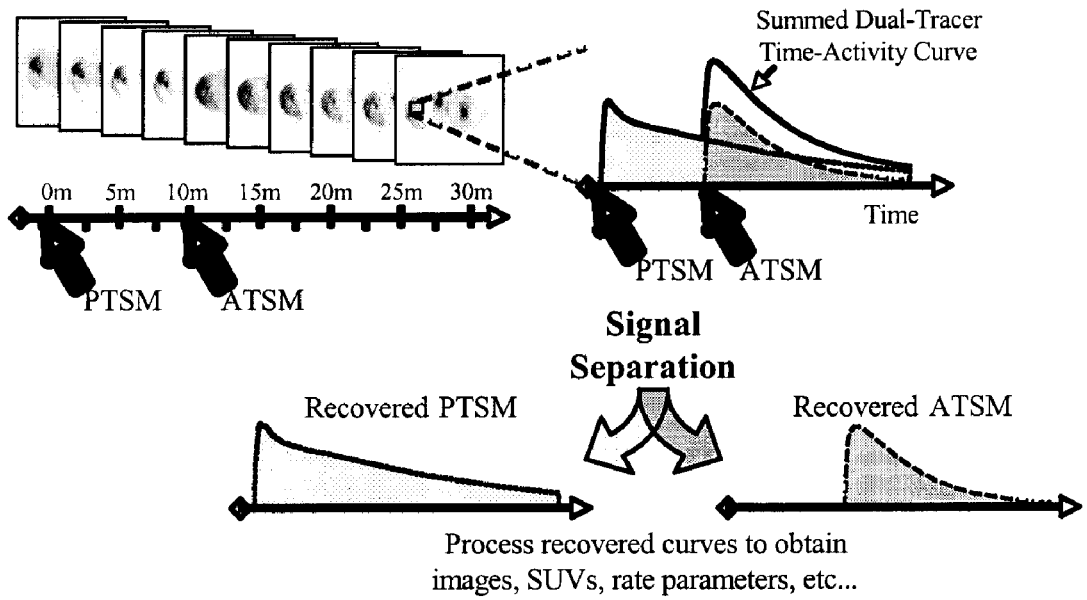
FIG. 11 illustrates exemplary methods for imaging multiple PET tracers in a single scan with staggered injections, where imaging measures for each tracer are separated and recovered based on differences in tracer kinetic behavior and radioactive decay.

In another exemplary application according to embodiments of the present invention, an evaluation of rapid dual-tracer $^{62}$Cu-PTSM+$^{62}$Cu-ATSM PET was performed in subjects (dogs) having spontaneously-occurring tumors. Described in this example are methods for imaging multiple PET tracers in a single scan with staggered injections, where imaging measures for each tracer are separated and recovered based on differences in tracer kinetic behavior and radioactive decay, as shown in FIG. 11

The accuracy and noise properties of rapid dual-tracer blood flow and hypoxia imaging protocols were studied using a series of simulated datasets, leading to an optimized protocol for imaging both tracers in a single 30 min. scan. Blood flow and hypoxia are complex inter-related factors, and imaging both together can provide complementary information to help guide treatment selection, planning, and early response monitoring. A number of tracers may be considered for imaging tumor blood flow and hypoxia, including the chemical analogues copper-pyruvaldehyde-bis[N4-methylthiosemicarbazone] and Cu-diacetyl-bis[N4-methylthiosemicarbazone] (PTSM and ATSM, respectively). While PTSM distributes in proportion to blood flow and is rapidly reduced and trapped in tissues, ATSM has a lower redox potential and is selectively retained in hypoxic tissues. Unlike many hypoxia tracers, ATSM clears quickly from normoxic tissues and may delineate hypoxic regions within 15-20 min after injection. However, the images in such timeframes also contain significant flow-dependence, an issue which may potentially be resolved by concurrent imaging of blood flow and hypoxia using dual-tracer techniques. Several positron-emitting copper isotopes can be used to label these tracers, with half-lives raging from 9.7 m to 12.7 hr. The shortest-lived of these, $^{62}$Cu, is produced using a portable $^{62}$Zn/$^{62}$Cu generator, providing on-demand availability that simplifies the logistics of tracer synthesis and delivery for dual-tracer studies.

Described herein is an exemplary application of rapid dual-tracer $^{62}$Cu-PTSM+$^{62}$Cu-ATSM imaging in a large-animal tumor model, where measures from rapid dual-tracer imaging were evaluated and compared using separately acquired, single-tracer scans as the standard. Since the tracer-recovery signal separation procedure relies upon differences in tracer kinetics, experimental evaluation of the rapid multi-tracer technique requires a physiologic model with appropriate distribution kinetics. Likewise, in comparing rapid dual-tracer imaging to conventional single-tracer imaging, separate scans with each tracer and accurate co-registration are needed. The following sections describe the experimental setup, data processing and analysis methods, and results of linear regression analysis comparing static and dynamic imaging measures recovered from rapid dual-tracer PTSM+ATSM imaging versus separate, single-tracer imaging.

A. Methods Utilized in Second Example

PET scanning. Each subject (e.g., dog) described herein received separate single-tracer scans with $^{62}$Cu-PTSM and $^{62}$Cu-ATSM, with a delay of 90 min or greater between scans so that residual activity from the previous injection had decayed to less than 0.2% of the injected value. Since the objective of the study was to evaluate rapid dual-tracer imaging measures using conventional single-tracer scans as the standard for comparison, a dual-tracer "emulation" protocol was used as previously described herein, namely single-tracer scans were acquired using the dual-tracer scanning protocol, and the raw scanner data were then combined to create an emulated dual-tracer dataset. This provided paired single- and dual-tracer data where the components of the dual-tracer data exactly matched the single-tracer standards, permitting a direct evaluation of the tracer-recovery signal separation algorithm.

Figure 12:
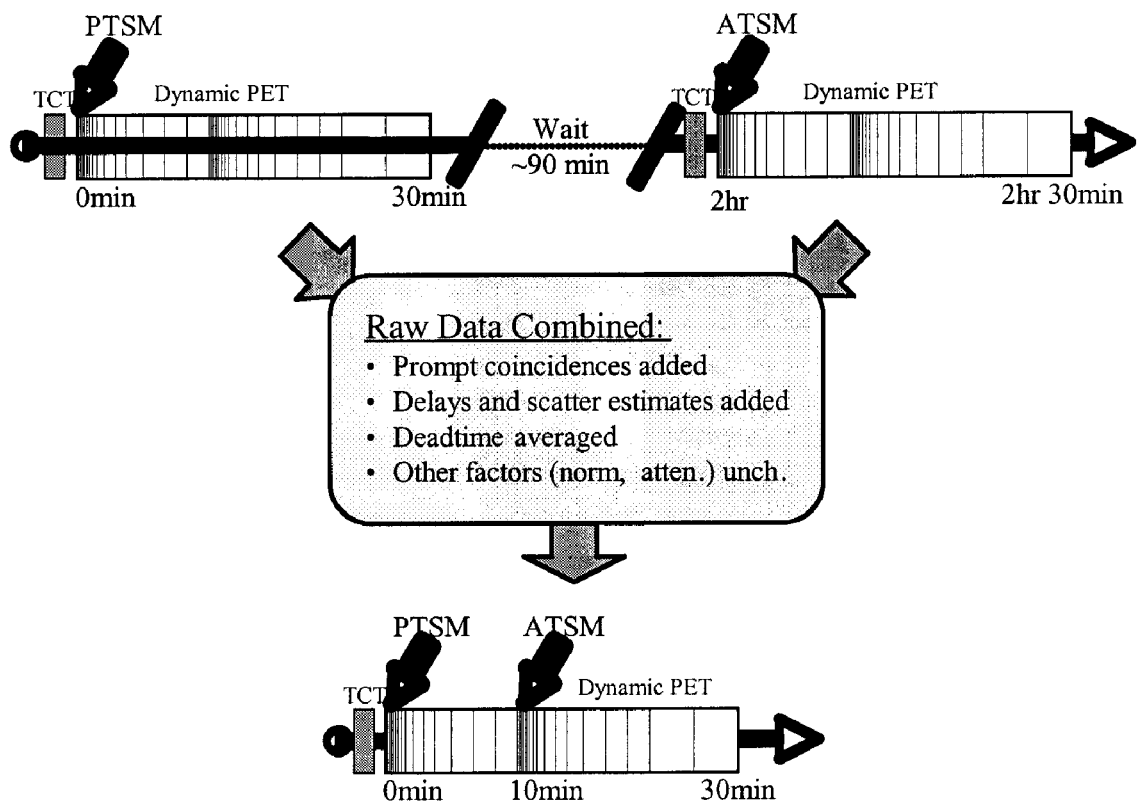
FIG. 12 provides an overview of the experimental approach according to an embodiment of the present invention.

FIG. 12 provides an overview of the experimental approach according to an embodiment of the present invention. A 10 min. transmission scan was performed prior to injection of each tracer for attenuation correction and to detect any misalignment between scans (none noted). The emulated dual-tracer scan had PTSM injected at time 0 and ATSM injected at 10 min. according to the protocol described above. Dynamic scanning was performed, starting with rapid sampling at the time of injection (5 sec. timeframes), followed by progressively slower sampling as tracer distribution slowed and stabilized. At 10 min. after injection of PTSM, the sequence with fast sampling was restarted for the ATSM injection. The complete temporal sampling schedule was: 12×5 s, 6×10 s, 6×30 s, 5×60 s, 12×5 s, 6×10 s, 6×30 s, 5×60 s, 5×120 s, for a total scan duration of 30 ml. $^{62}$Cu-PTSM and $^{62}$Cu-ATSM were prepared using a portable $^{62}$Zn/$^{62}$Cu generator and tracer preparation kits obtained from, for example, Proportional Technologies (Houston, Tex.). Administered radioactivity for PTSM and ATSM were 4.7±3.2 and 5.1±2.8 mCi, respectively. After completing the PTSM and ATSM scans, whole-body imaging with $^{18}$F-fluorodeoxyglucose (FDG) was also performed to aid in tumor identification and localization.

Arterial blood sampling. Blood samples (approximately 0.4-0.5 ml) were drawn from an AV shunt on a schedule similar to the scanning schedule for determination of the arterial input functions. Since PTSM and ATSM bind to serum albumin (Herrero et al., 1996, Lewis et al., 2002), the samples at roughly 1 min intervals were added to 1.0 ml octanol in test tubes and centrifuged to separate the freely available (octanol separated) and bound (pellet) fractions. Each sample was weighed and counted in a well counter soon after withdrawal, and corrections for radioactive decay were applied to recover time-activity curves for the whole-blood and freely-available arterial input functions for use with compartment modeling. For the actual-dual tracer scan, activity from both tracers was present in the blood once ATSM was administered. While this could potentially complicate measurement of the input function for each tracer; however, at 10 min. after injection the octanol-extractable fraction of PTSM in the blood was only ~1%, with the remaining activity albumin bound. Thus, while the whole-blood activity contained contributions from each tracer, the octanol-extractable input function for ATSM was not significantly contaminated by the PTSM injection.

Reconstruction and processing. After all imaging was completed, the raw data including all corrections and normalizations were offloaded for subsequent processing. For each subject (e.g., dog), three datasets were prepared for reconstruction: single-tracer PTSM, single-tracer ATSM, and emulated dual-tracer PTSM+ATSM, where the final dataset was formed by combining the raw data for each of the single-tracer scans as in FIG. 12. Each dataset was reconstructed using four iterations of ordered-subsets expectation-maximization (OSEM) with twelve subsets, where the raw line-of-response (LOR) data were reconstructed directly and all corrections—including arc correction—were incorporated into the reconstruction matrix (LOR-OSEM, (Kadrmas, 2004)). No reconstruction filter was applied. Forty-seven regions-of-interest (ROIs), 4.5±4.6 cm$^3$, were drawn on 10 tumor sites identified on the images, where multiple ROIs were used to characterize heterogeneity of larger tumors. Time-activity curves for each ROI and dataset were obtained, and the dual-tracer curves were processed by the signal separation procedure described below to recover both static and dynamic imaging measures for each tracer.

B. Dual-Tracer Signal Separation

Figure 13:
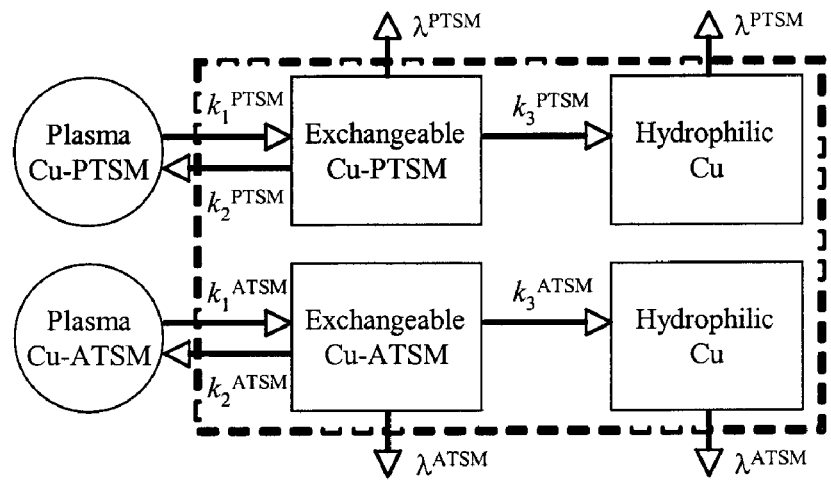
FIG. 13 is an illustration of a combined compartment model, whereby the kinetics of both PTSM and ATSM were assumed to follow compartment models with two tissue compartments and three rate parameters.

As described herein, the kinetics of both PTSM and ATSM were assumed to follow compartment models with two tissue compartments and three rate parameters as shown in FIG. 13. The second compartment for each tracer had irreversible trapping, and radioactive decay was explicitly incorporated into the kinetic model to aid in signal separation. While the primary purpose of the kinetic model as used herein is for dual-tracer signal separation, and not necessarily to quantify kinetic rate parameters, it is to be recognized that rate parameters are obtained as a byproduct of the signal separation algorithm. Because accurate quantification of the rate parameters is not necessary, the level of accuracy required in the input functions can be greatly reduced as compared to usual applications of compartment models when the recovered curves for each tracer are processed to obtain static imaging measures (e.g. standardized uptake value, SUV).

Under these compartment models, the activity concentration A(t) of the extravascular tissue compartments for each tracer can be written:

$$A^*(t) = \left\{ \frac{k_1^*}{k_2^* + k_3^*} [k_3^* e^{-\lambda^* t} + k_2^* e^{-(k_2^* + k_3^* + \lambda^*)t}] \right\} \otimes b^*(t), \quad (18)$$

where $\{k_i\}$ are the rate constants, $\lambda$ is the radioactive decay constant, b(t) is the input function (concentration of freely exchangeable tracer in the blood), $\otimes$ is the convolution operator, and * is used to denote either PTSM or ATSM since the same model was used for each. For dual-tracer data, $b^{ATSM}(t)$ was zero until ATSM was injected (t=10 min). The activity concentration $R^{Dual}(t)$ in a ROI measured by PET for dual-tracer data is modeled as:

$$R^{Dual}(t) = f_B B(t) + (1 - f_B)[A^{PTSM}(t) + A^{ATSM}(t)], \quad (19)$$

where $f_B$ is the vascular fraction in the ROI and B(t) is the total activity concentration in the whole blood (including both tracers when present).

Figure 14:
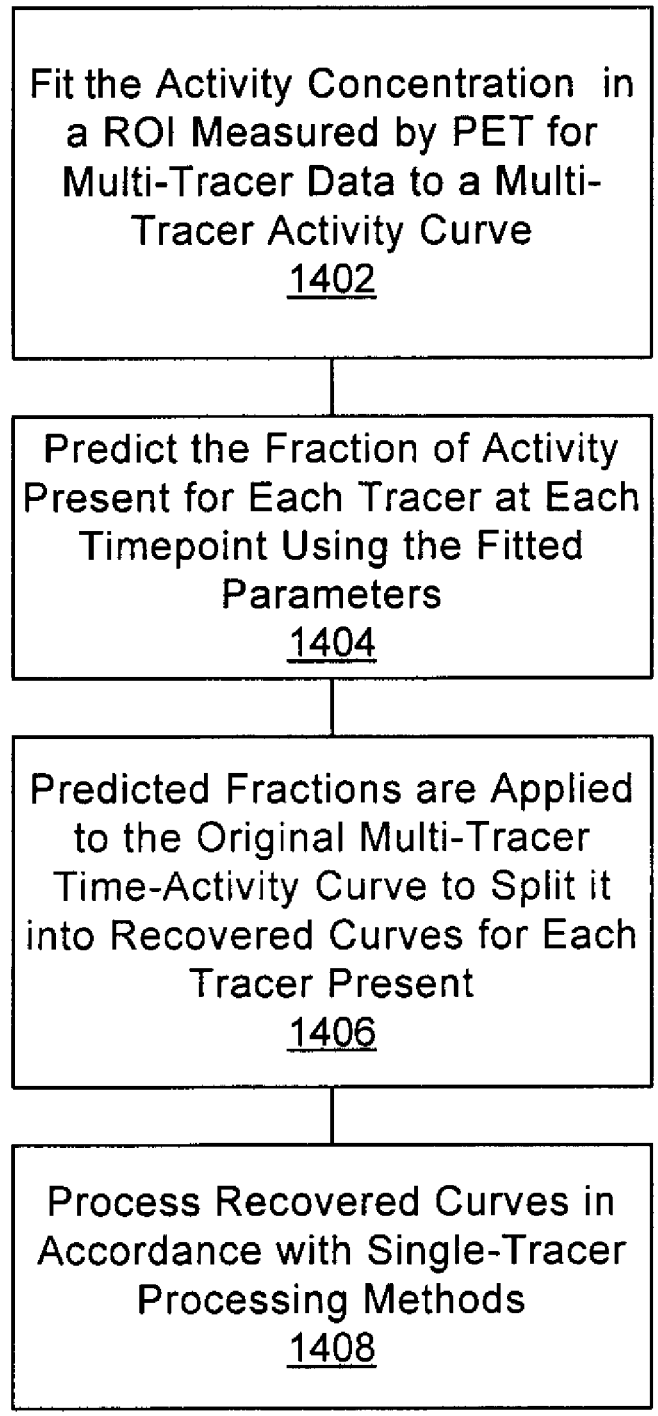
FIG. 14 illustrates an exemplary process for signal separation from combined multi-tracer PET data.

Signal Separation Algorithm. An exemplary process for signal separation from combined multi-tracer PET data is shown in FIG. 14. At step 1402 of the process, the signal separation algorithm begins by fitting equation 19 to the dual-tracer (or multi-tracer) time-activity curve. As described herein, the fits were performed via Levenberg-Marquardt minimization of chi-squared, though other curve-fitting methods are contemplated within the scope of this invention. At step 1404, the fitted parameters ($\{k_i^{PTSM}\}$, $\{k_i^{ATSM}\}$, $f_B$) are used to predict the fraction of activity present for each tracer at each timepoint. At step 1406, the predicted fractions are applied to the original (noisy) multi-tracer time-activity curve according to previously provided equation (8) in order to split it into recovered curves for each tracer present, for example one curve for PTSM and one for ATSM. At step 1408 the recovered curves are then processed in whatever manner desired according to usual single-tracer processing methods. Here, they were integrated to obtain SUVs for each tracer, and the kinetic rate parameters themselves were also analyzed and compared to those from single-tracer time-activity curves.

C. Analysis

Linear regression analysis was used to compare the results from dual-tracer imaging to those from the separate, single-tracer scans. Thus, the analysis tests whether the same results can be obtained from rapid dual-tracer imaging as from single-tracer imaging, but does not approach the question of how accurately PTSM and ATSM measure blood flow and hypoxia. Three sets of quantitative measures were analyzed for each tracer: (i) the SUV obtained by integrating the time-activity curve, with decay correction, from 15 to 20 min. post-injection; (ii) the wash-in rate parameter, $k_1$, obtained from the compartment model fits; and (iii) the net uptake parameter, $k_{net} = k_1 k_3 / (k_2 + k_3)$. For PTSM, each of these three measures would have potential use for characterizing blood flow; and for ATSM, the SUV and net uptake would relate to hypoxia (though consideration of flow-dependent tracer delivery would be necessary to obtain a direct measure of hypoxia). These three imaging measures provide well-defined parameters for evaluating the performance of the signal separation algorithm.

D. Results

Figure 15:
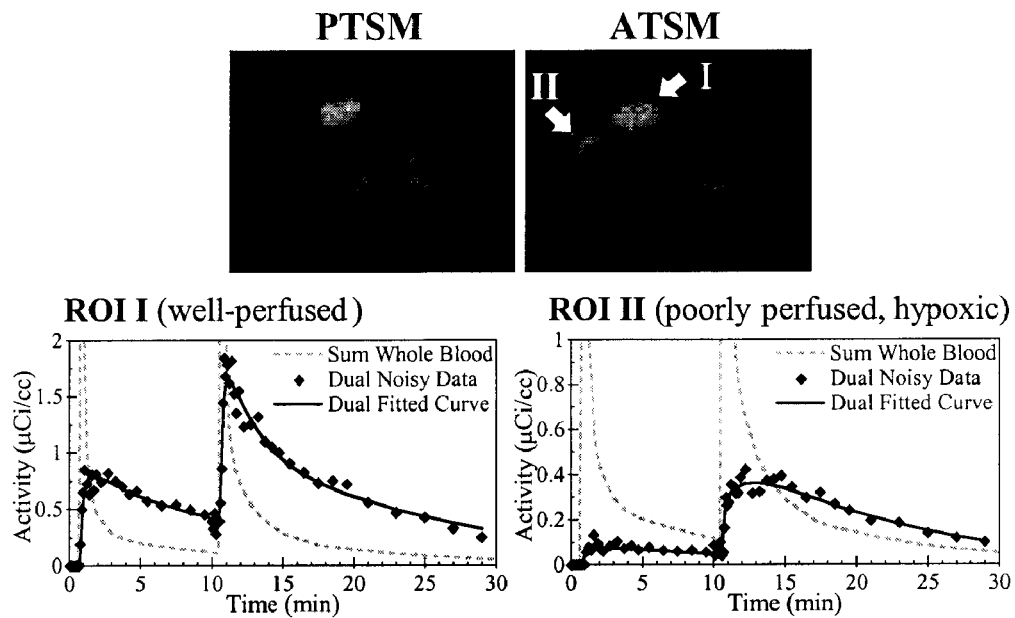
FIG. 15 shows example PTSM and ATSM images and time-activity curves for a 28.0 kg female Labrador retriever with histologically proven mammary papillary cystadenocarcinoma.
Figure 16:
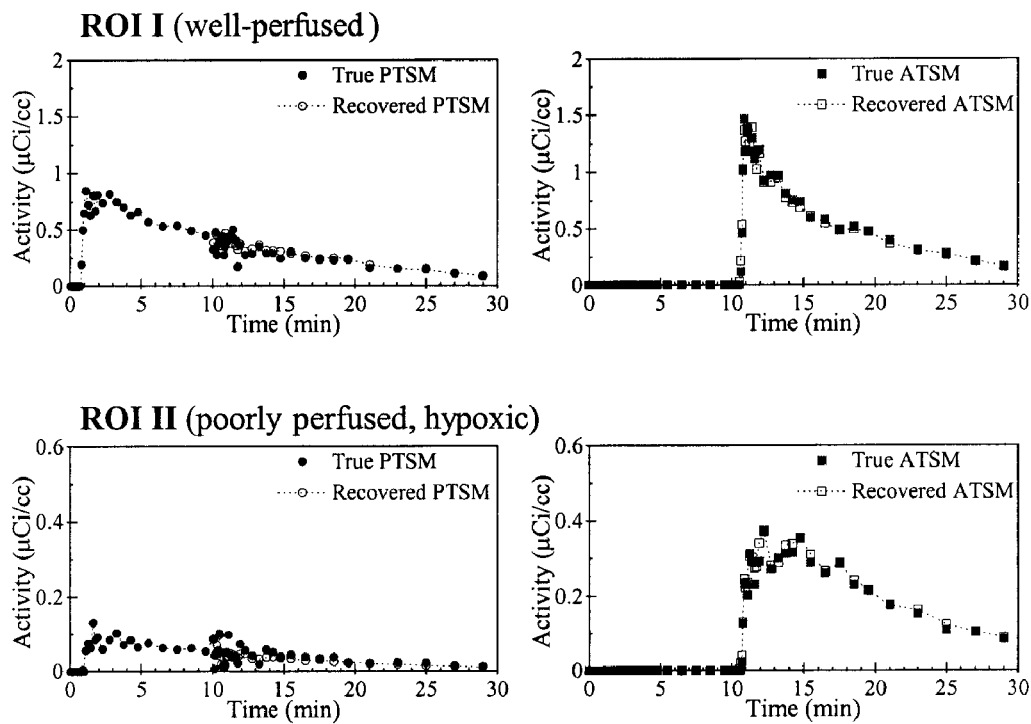
FIG. 16 illustrates time-activity curves from dual-tracer imaging for two regions presented in FIG. 15 recovered according to an embodiment of the present invention, where the standard single-tracer curves are also shown for comparison.

The experiments were successfully carried out for each of the four dogs studied in this work. FIG. 15 shows example PTSM and ATSM images and time-activity curves for a 28.0 kg female Labrador retriever with histologically proven mammary papillary cystadenocarcinoma. A large tumor (I) is seen toward the top of field with strong uptake of both tracers and relatively fast ATSM washout. A secondary tumor region is also evident (II) which has markedly lower tracer uptake but prolonged retention of ATSM, consistent with an underperfused hypoxic region. The recovered time-activity curves from dual-tracer imaging for these two regions are presented in FIG. 16, where the standard single-tracer curves are also shown for comparison. There is excellent agreement between the recovered and standard curves, with greatest discrepancy in the noisy (5 sec.) timeframes at 10 min. corresponding to the injection of ATSM.

FIGS. 17A and 17B show scatters plots of SUVs for PTSM and ATSM recovered from dual-tracer data versus the single-tracer standards. Linear regression analysis showed excellent correlation between dual- and single-tracer results, with correlation coefficients of 0.98 and 0.99 for PTSM and ATSM, respectively. Low and high SUVs for each tracer were well differentiated, with the PTSM SUV being somewhat overestimated for dual-tracer and ATSM somewhat underestimated. These results demonstrate recovery of static imaging measures with good accuracy, though the moderate bias present suggests that improvements in the signal separation algorithm may be warranted.

The results for kinetic parameter estimates are shown in FIGS. 18A-18D. Excellent agreement in $k_1$ estimates was obtained for both tracers (R>0.99), demonstrating that measurement of the wash-in phase of each tracer is not degraded by rapid dual-tracer imaging. Since there was no ATSM activity present during the PTSM wash-in phase, this result is unsurprising; however, the greatest overlap of activity occurs during the ATSM wash-in phase, and the result that ATSM $k_1$ is accurately recovered is promising. Very good agreement was also observed for the net uptake parameters for each tracer, with some overestimation for PTSM and under-estimation for ATSM (slopes 1.08 and 0.88, respectively). Wash-out of ATSM was also recovered with good accuracy (R=0.94), which is of consequence since retention versus wash-out of ATSM distinguishes between hypoxic and normoxic tissues.

The dual-tracer signal separation procedure was also applied to the actual dual-tracer scan performed in one of the dogs. Though a robust standard was not available for evaluating the accuracy of the recovered PTSM and ATSM data for this scan, the recovered curves were comparable to the single-tracer curves. Correlation coefficients for SUVs, $k_1$, $k_{net}$, and $k_2^{ATSM}$ for dual-tracer versus single-tracer ranged from 0.84-0.96, where these results contain differences due to reproducibility of imaging the same tracer 4-5 hours apart as well as differences due to the dual-tracer technique. This scan demonstrates actual implementation of the dual-tracer technique with results consistent with the other results of this example.

Methods of Use

Figure 19:
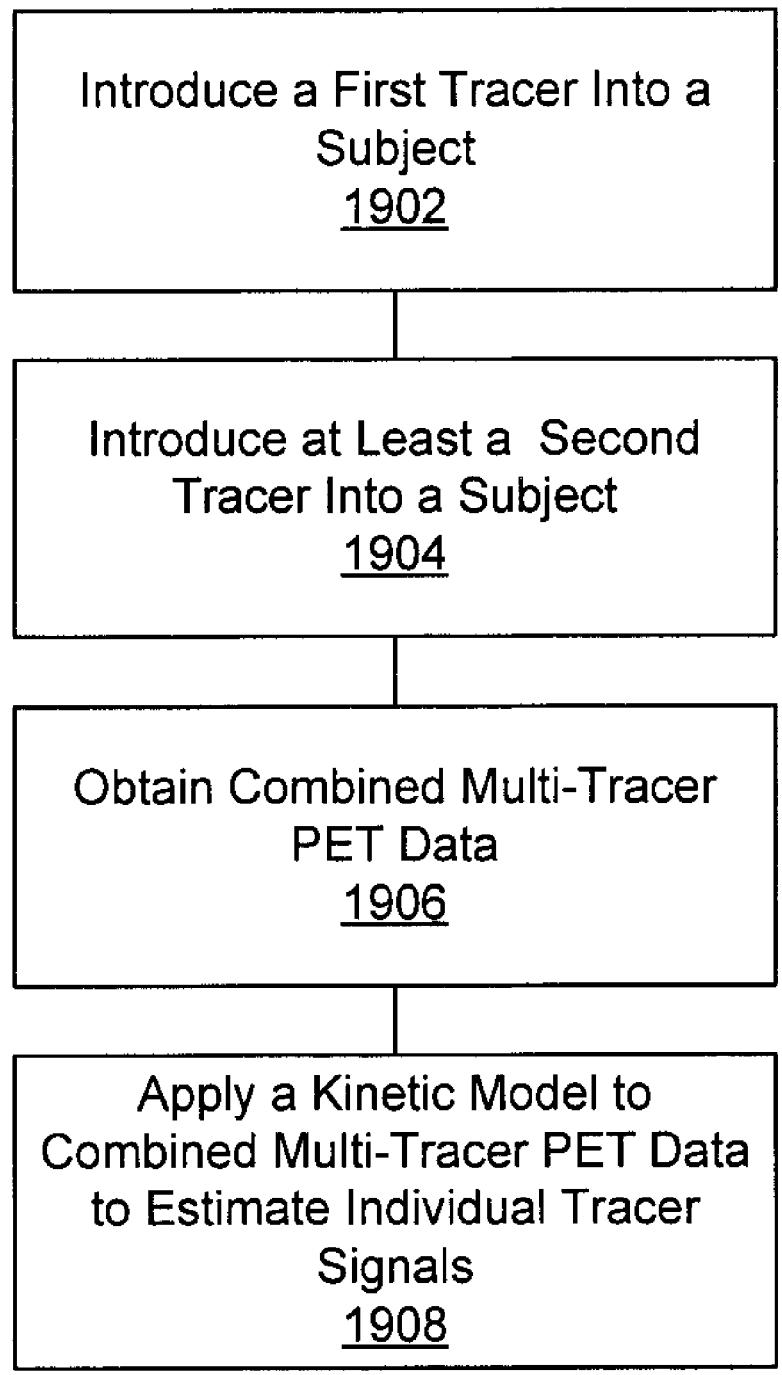
FIG. 19 is a flow chart illustrating an exemplary process for recovering individual tracer signals from multi-tracer PET data according to the signal separation algorithm described herein.

FIG. 19 is a flow chart illustrating an exemplary process for recovering individual tracer signals from multi-tracer PET data according to the signal separation algorithm described herein. At step 1902, a first tracer is introduced into a subject. As indicated herein, these tracers can be, for example, $^{13}N$, ATSM, or PTSM among others now-developed or developed in the future. At step 1904, a second tracer is introduced into the subject. This step can be repeated for however many tracers are to be used in the process. At step 1906, a PET scan is performed on all or a part of the subject to obtain combined multi-tracer PET data. At step 1908, a kinetic model is applied to the combined multi-tracer PET data to estimate individual tracer signals.

In various aspects, the process of FIG. 19 can be applied for cardiac imaging (as described herein) and for cancer imaging. In some instances, one or more of the tracers used for cancer imaging comprise FDG.

CONCLUSION

While this invention has been described in connection with preferred embodiments and specific examples, it is not intended that the scope of the invention be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

REFERENCES

Bland J M and Altman D G 1986 Statistical methods for assessing agreement between two methods of clinical measurement *Lancet* 1 307-10.

Bol A et al 1993 Direct comparison of [$^{13}N$]ammonia and [$^{15}O$]water estimates of perfusion with quantification of regional myocardial blood flow by microspheres *Circulation* 87 5 12-25.

Bormans G et al 1995 Metabolism of nitrogen-13 labelled ammonia in different conditions in dogs, human volunteers and transplant patients *Eur. J. Nucl. Med.* 22 116-21.

Bruehlmeier, M., Roelcke, U., Schubiger, P. A. & Ametamey, S. M. (2004) Assessment of hypoxia and perfusion in human brain tumors using PET with 18F-fluoromisonidazole and 15O—H2O. *J. Nuc. Med.*, 45, 1851-9.

Chang J Y, Duara R, Barker W, Apicella A and Finn R 1987 Two behavioral states studied in a single PET/FDG procedure: theory, method, and preliminary results *J. Nucl. Med.* 28 852-60.

Chang J Y, Duara R, Barker W, Apicella A, Yoshii F, Kelley R E, Ginsberg M D and Boothe T E 1989 Two behavioral states studied in a single PET/FDG procedure: error analysis *J. Nucl. Med.* 30 93-105.

Choi Y, Huang S C, Hawkins R A, Kim J Y, Kim B T, Hoh C K, Chen K, Phelps M E and Schelbert H R 1999 Quantification of myocardial blood flow using 13N-ammonia and PET: comparison of tracer models *J. Nucl. Med.* 40 1045-55.

Converse A K, Barnhart T E, Dabbs K A, DeJesus O T, Larson J A, Nickles R J, Schneider M L and Roberts A D 2004 PET measurement of rCBF in the presence of a neurochemical tracer *J. Neurosci. Methods* 132 199-208.

Dehdashti, F., Mintun, M. A., Lewis, J. S., Bradley, J., Govindan, R., Laforest, R., Welch, M. J. & Siegel, B. A. (2003) In vivo assessment of tumor hypoxia in lung cancer with 60Cu-ATSM. *Eur. J. Nuc. Med. Mol. Imaging*, 30, 844-50.

Delforge J, Syrota A and Mazoyer B M 1990 Identifiability analysis and parameter identification of an in vivo ligand-receptor model from PET data *IEEE Trans. Biomed. Eng.* 37 653-61.

Flower, M. A., Zweit, J., Hall, A. D., Burke, D., Davies, M. M., Dworkin, M. J., Young, H. E., Mundy, J., Ott, R. J., Mccready, V. R., Carnochan, P. & Allen-Mersh, T. G. (2001) $^{62}$Cu-PTSM and PET used for the assessment of angiotensin II-induced blood flow changes in patients with colorectal liver metastases. *Eur. J. Nucl. Med.*, 28, 99-103.

Fujibayashi, Y., Taniuchi, H., Yonekura, Y., Ohtani, H., Konishi, J. & Yokoyama, A. (1997) Copper-62-ATSM: a new hypoxia imaging agent with high membrane permeability and low redox potential. *J. Nucl. Med.*, 38, 1155-60.

Haynes, N. G., Lacy, J. L., Nayak, N., Martin, C. S., Dai, D., Mathias, C. J. & Green, M. A. (2000) Performance of a $^{62}$Zn/$^{62}$Cu generator in clinical trials of PET perfusion agent $^{62}$Cu-PTSM. *J. Nucl. Med.*, 41, 309-14.

Herrero, P., Hartman, J. J., Green, M. A., Anderson, C. J., Welch, M. J., Markham, J. & Bergmann, S. R. (1996) Regional myocardial perfusion assessed with generator-produced copper-62-PTSM and PET. *J. Nucl. Med.*, 37, 1294-300.

Huang S C, Bahn M M, Barrio J R, Hoffman J M, Satyamurthy N, Hawkins R A, Mazziotta J C and Phelps M E 1989 A double-injection technique for in vivo measurement of dopamine D2-receptor density in monkeys with 3-(2'-[18F]fluoroethyl)spiperone and dynamic positron emission tomography *J. Cereb. Blood Flow Metab.* 9 850-8.

Huang, S. C., Carson, R. E., Hoffman, E. J., Kuhl, D. E. & Phelps, M. E. (1982) An investigation of a double-tracer technique for positron computerized tomography. *J. Nucl. Med.*, 23, 816-22.

Hutchins G D, Schwaiger M, Rosenspire K C, Krivokapich J, Schelbert H and Kuhl D E 1990 Noninvasive quantification of regional blood flow in the human heart using N-13 ammonia and dynamic positron emission tomographic imaging *J. Am. Coll. Cardiol.* 15 1032-42.

Ikoma, Y., Toyama, H., Uemura, K. & Uchiyama, A. (2001) Evaluation of the reliability in kinetic analysis for dual tracer injection of FDG and flumazenil PET study. IN SEIBERT, J. A. (Ed.) *Conf. Rec. IEEE Nuc. Sci. Symp. and Med. Imaging Conf.* Piscataway, N.J., USA, IEEE.

Kadrmas, D. J. (2004) LOR-OSEM: statistical PET reconstruction from raw line-of-response histograms. *Phys Med Biol*, 49, 4731-44.

Kadrmas, D. J. & Rust, T. C. (2005) Feasibility of Rapid Multi-Tracer PET Tumor Imaging. *IEEE Trans. Nucl. Sci.*, 52 134 1-7.

Kaufmann P A and Camici P G 2005 Myocardial blood flow measurement by PET: technical aspects and clinical applications *J. Nucl. Med.* 4675-88.

Koeppe, R. A., Ficaro, E. P., Raffel, D. M., Minoshima, S. & Kilbourn, M. R. (1998) Temporally overlapping dual-tracer PET studies. In Carson, R. E., Daube-Witherspoon, M. E. & Herscovitch, P. (Eds.) *Quantitative Functional Brain Imaging with Positron Emission Tomography*. San Diego, Calif., Academic Press.

Koeppe, R. A., Raffel, D. M., Snyder, S. E., Ficaro, E. P., Kilbourn, M. R. & Kuhl, D. E. (2001) Dual-[$^{11}$C]tracer single-acquisition positron emission tomography studies. *J. Cereb. Blood Flow Metab.*, 21, 1480-92.

Krivokapich J, Smith G T, Huang S C, Hoffman E J, Ratib O, Phelps M E and Schelbert H R 1989 13N ammonia myocardial imaging at rest and with exercise in normal volunteers. Quantification of absolute myocardial perfusion with dynamic positron emission tomography *Circulation* 80 1328-37.

Lehtio, K., Eskola, O., Viljanen, T., Oikonen, V., Gronroos, T., Sillanmaki, L., Grenman, R. & Minn, H. (2004) Imaging perfusion and hypoxia with PET to predict radiotherapy response in head-and-neck cancer. *Int. J. Rad. Oncol. Biol. Phys.*, 59, 971-82.

Lehtio, K., Oikonen, V., Gronroos, T., Eskola, O., Kalliokoski, K., Bergman, J., Solin, O., Grenman, R., Nuutila, P. & Minn, H. (2001) Imaging of blood flow and hypoxia in head and neck cancer: initial evaluation with [$^{(15)}$O]H(2)O and [$^{(18)}$F]fluoroerythronitroimidazole PET. *J. Nuc. Med.*, 42, 1643-52.

Lewis, J. S., Herrero, P., Sharp, T. L., Engelbach, J. A., Fujibayashi, Y., Laforest, R., Kovacs, A., Gropler, R. J. & Welch, M. J. (2002) Delineation of hypoxia in canine myocardium using PET and copper(II)-diacetyl-bis(N(4)-methylthiosemicarbazone). *J. Nucl. Med.*, 43, 1557-69.

Lewis, J. S., McCarthy, D. W., McCarthy, T. J., Fujibayashi, Y. & Welch, M. J. (1999) Evaluation of 64Cu-ATSM in vitro and in vivo in a hypoxic tumor model. *J. Nucl. Med.*, 40, 177-83.

Lewis, J. S., Sharp, T. L., Laforest, R., Fujibayashi, Y. & Welch, M. J. (2001) Tumor uptake of copper-diacetyl-bis (N(4)-methylthiosemicarbazone): effect of changes in tissue oxygenation. *J. Nucl. Med.*, 42, 655-61.

Mathias, C. J., Green, M. A., Morrison, W. B. & Knapp, D. W. (1994) Evaluation of Cu-PTSM as a tracer of tumor perfusion: comparison with labeled microspheres in spontaneous canine neoplasms. *Nucl. Med. Biol.*, 21, 83-7.

Mathias, C. J., Welch, M. J., Perry, D. J., Mcguire, A. H., Zhu, X., Connett, J. M. & Green, M. A. (1991) Investigation of copper-PTSM as a PET tracer for tumor blood flow. *Int. J. Rad. Appl. Instrum. B*, 18, 807-11.

Muzik O, Beanlands R S, Hutchins G D, Mangner T J, Nguyen N and Schwaiger M 1993 Validation of nitrogen13-ammonia tracer kinetic model for quantification of myocardial blood flow using PET *J. Nucl. Med.* 34 83-91.

Nagamachi S, Czernin J, Kim A S, Sun K T, Bottcher M, Phelps M E and Schelbert H R 1996 Reproducibility of measurements of regional resting and hyperemic myocardial blood flow assessed with PET *J. Nucl. Med.* 37 1626-31.

Nishizawa S, Kuwabara H, Ueno M, Shimono T, Toyoda H and Konishi J 2001 Double-injection FDG method to measure cerebral glucose metabolism twice in a single procedure *Ann. Nucl. Med.* 15203-7.

Nitzsche E U, Choi Y, Czernin J, Hoh C K, Huang S C and Schelbert H R 1996 Noninvasive quantification of myocardial blood flow in humans. A direct comparison of the [$^{13}$N]ammonia and the [$^{15}$O]water techniques *Circulation* 93 2000-6.

Press W H, Flannery B P, Teukolsky S A and Vetterling W T 1992 *Numerical Recipes in C* (Cambridge: Cambridge University Press).

Rajendran, J. G. & Krohn, K. A. (2005) Imaging hypoxia and angiogenesis in tumors. *Radiol. Clin. North Am.,* 43, 169-87.

Rosenspire K C, Schwaiger M, Mangner T J, Hutchins G D, Sutorik A and Kuhl D E 1990 Metabolic fate of [$^{13}$N] ammonia in human and canine blood *J. Nucl. Med.* 31 163-7.

Rust, T. C., Dibella, E. V., Mcgann, C. J., Christian, P. E., Hoffman, J. M. & Kadrmas, D. J. (2006) Rapid dual-injection single-scan 13N-ammonia PET for quantification of rest and stress myocardial blood flows. *Phys Med Biol,* 51, 5347-62.

Rust, T. C. & Kadrmas, D. J. (2006) Rapid dual-tracer PTSM+ATSM PET imaging of tumour blood flow and hypoxia: a simulation study. *Phys Med Biol,* 51, 61-75.

Schelbert H R, Beanlands R, Bengel F, Knuuti J, DiCarli M, Machac J and Patterson R 2003 PET myocardial perfusion and glucose metabolism imaging: Part 2. Guidelines for interpretation and reporting *J. Nucl. Cardiol.* 10 557-71.

Takahashi, N., Fujibayashi, Y., Yonekura, Y., Welch, M. J., Waki, A., Tsuchida, T., Sadato, N., Sugimoto, K. & Itoh, H. (2000) Evaluation of 62Cu labeled diacetyl-bis(N4-methylthiosemicarbazone) as a hypoxic tissue tracer in patients with lung cancer. *Ann. Nucl. Med.,* 14, 323-8.

What is claimed is:

1. A method of recovering individual tracer signals from multi-tracer PET data comprising:

introducing a plurality of tracers into a subject, wherein the plurality of tracers comprise a first tracer and at least a second tracer;

obtaining multi-tracer PET data of the subject by performing a PET scan of the subject substantially concurrently or subsequent to introducing the first tracer and continuing at least a portion of the time after the introduction of the at least second tracer into the subject;

providing a multi-tracer kinetic model, wherein said multi-tracer kinetic model estimates parameters or a time-dependent activity timecourse for each of said first and at least second tracer;

applying said multi-tracer PET data to said multi-tracer kinetic model and estimating individual tracer signals for each of said first tracer and at least second tracer at one or more timepoints based upon a fit of the multi-tracer PET data to the multi-tracer kinetic model; and applying said multi-tracer kinetic model to individual voxels or groups of voxels to recover static images for each of said first tracer and said at least second tracer, wherein said static images comprise rest or stress cardiac images.

2. The method of claim 1, wherein the multi-tracer kinetic model is at least comprised in part of a compartment model for one or more of said first tracer and said at least second tracer.

3. The method of claim 1, wherein the multi-tracer kinetic model is at least comprised in part of an input function convolved with one or more exponentials for one or more of said first tracer and said at least second tracer.

4. The method of claim 1, wherein the multi-tracer kinetic model is at least comprised in part of a linear or non-linear summing of kinetic components for one or more of the first tracer and the at least second tracer.

5. The method of claim 4, wherein the kinetic components are obtained from methods including principal component analysis (PCA), independent component analysis (ICA), frequency analysis of dynamic structures (FADS), or Karhunen-Loeve (KL) transforms of either modeled or empirically determined populations.

6. The method of claim 1, wherein applying said multi-tracer PET data to said multi-tracer kinetic model and estimating individual tracer signals for each of said first tracer and said at least second tracer at one or more timepoints from the multi-tracer PET data based upon a fit of the multi-tracer PET data to the multi-tracer kinetic model comprises breaking apart said multi-tracer PET data into said individual tracer signals at each of said one or more timepoints using a proportional contribution of each of said first tracer and said at least second tracer at each of said one or more timepoints such that the individual tracer signals form a recovered dynamic/multi-timepoint PET signal for each tracer.

7. The method of claim 1 further comprising processing said individual tracer signals for each of said first tracer and said at least second tracer to obtain static imaging measures for each of said first tracer and said at least second tracer.

8. The method of claim 7, wherein said static imaging measures include standardized uptake value (SUV).

9. The method of claim 7 further comprising applying said multi-tracer kinetic model to individual voxels or groups of voxels to recover dynamic images for each of said first tracer and said at least second tracer.

10. The method of claim 9, wherein the static imaging measures include standardized uptake value (SUV).

11. The method of claim 9, wherein said dynamic images comprise rest or stress cardiac images.

12. The method of claim 11, wherein the static imaging measures include standardized uptake value (SUV).

13. The method of claim 9, wherein said dynamic images comprise cancer imaging.

14. The method of claim 13, wherein the static imaging measures include standardized uptake value (SUV).

15. The method of claim 9, wherein the recovered dynamic images for each tracer are further processed to obtain static imaging measures for each of said first tracer and said at least second tracer.

16. The method of claim 1, wherein said static images comprise cancer imaging.

17. The method of claim 1, wherein two or more of the plurality of tracers are the same.

18. The method of claim 1, wherein two or more of the plurality of tracers are different.

19. The method of claim 1, wherein one of the plurality of tracers is FDG and said method is used for cancer imaging.

20. A method of recovering individual tracer signals from multi-tracer PET data for rest/stress cardiac imaging comprising:

introducing a plurality of tracers into a subject, wherein said plurality of tracers comprise at least a first tracer introduced into the subject during cardiac rest and at least a second tracer introduced into the subject during cardiac stress;

obtaining cardiac multi-tracer PET data of the subject by performing a cardiac PET scan of the subject concurrently or subsequent to introducing the plurality of tracers into the subject, wherein said cardiac multi-tracer PET data includes at least cardiac rest first tracer data and cardiac stress second tracer data;

providing a multi-tracer kinetic model, wherein said multi-tracer kinetic model estimates time-dependent kinetic parameters or a time-dependent activity timecourse for each of said plurality of tracers;

applying said cardiac multi-tracer PET data to said multi-tracer kinetic model and estimating individual tracer signals for each of said plurality of tracers at one or more timepoints based upon a fit of the multi-tracer PET data to the multi-tracer kinetic model; and applying said multi-tracer kinetic model to individual voxels or groups of voxels to recover dynamic or static cardiac images for each of said at least first tracer and said at least second tracer.

21. The method of claim 20, wherein the multi-tracer kinetic model is at least comprised in part of a compartment model for said first tracer and said second tracer and an uptake rate parameter ($K_1$), a net uptake rate parameter ($K_i$), or other parameter is recovered from the cardiac multi-tracer PET data for each of said plurality of tracers.

22. The method of claim 21 further comprising applying a background subtraction technique, wherein said background subtraction technique is used to correct or compensate the cardiac stress second tracer data for the presence of residual cardiac rest first tracer data.

23. The method of claim 22 wherein the static or dynamic cardiac images for said first tracer includes rest blood input and said rest blood input is extrapolated through and beyond the time the at least second tracer is introduced into the subject during cardiac stress.

24. The method of claim 20, wherein the multi-tracer kinetic model is at least comprised in part of an input function convolved with one or more exponentials for one or more of said plurality of tracers.

25. The method of claim 20, wherein the multi-tracer kinetic model is at least comprised in part of a linear or non-linear summing of kinetic components for one or more of the plurality of tracers.

26. The method of claim 25, wherein the kinetic components are obtained from methods including principal component analysis (PCA), independent component analysis (ICA), frequency analysis of dynamic structures (FADS), or Karhunen-Loeve (KL) transforms of either modeled or empirically determined populations.

27. The method of claim 20, wherein applying said cardiac multi-tracer PET data to said multi-tracer kinetic model and estimating individual tracer signals for each of said plurality of tracers at one or more timepoints from the multi-tracer PET data based upon a fit of the cardiac multi-tracer PET data to the multi-tracer kinetic model comprises breaking apart said cardiac multi-tracer PET data into said individual tracer signals at each of said one or more timepoints using a proportional contribution of each of said plurality of tracers at each of said one or more timepoints such that the individual tracer signals form a recovered dynamic/multi-timepoint PET signal for each tracer.

28. The method of claim 20 further comprising processing said individual tracer signals for each of said plurality of tracers to obtain static imaging measures for each tracer.

29. The method of claim 28, wherein said static imaging measures include standardized uptake value (SUV).

30. The method of claim 20, wherein said dynamic images comprise rest or stress cardiac images.

31. The method of claim 20, wherein the recovered dynamic images for each tracer are further processed to obtain static imaging measures for each of said plurality of tracers.

32. The method of claim 31, wherein the static imaging measures include standardized uptake value (SUV).

33. The method of claim 20, wherein said static images comprise rest or stress cardiac images.

34. The method of claim 20, wherein at least two of the plurality of tracers are the same.

35. The method of claim 20, wherein at least two of the plurality of tracers are different.

36. The method of claim 20, wherein applying said multi-tracer kinetic model to individual voxels or groups of voxels to recover dynamic or static cardiac images for each of said at least first tracer and said at least second tracer comprises imaging cardiac flow and viability.

37. The method of claim 20, where a third tracer such as $^{18}$F-fluorodeoxyglucose is also introduced into the subject and used to measure cardiac viability or other function in addition to the rest and stress blood flow tracers.

* * * * *